United States Patent [19]

Shiino et al.

[11] Patent Number: 4,537,648
[45] Date of Patent: Aug. 27, 1985

[54] AUTOMATIC SPECIMEN SEALING SYSTEM

[75] Inventors: Kouji Shiino; Nobuo Hashimoto; Shozo Wada, all of Tokyo; Keijiro Nakamura; Akio Izumi, both of Kanagawa; Toshio Sato, Kanagawa; Takashi Matsui, Tokyo, all of Japan

[73] Assignees: Sankyo Company Limited; Fuji Electric Company Ltd., both of Japan

[21] Appl. No.: 584,289

[22] Filed: Feb. 28, 1984

[30] Foreign Application Priority Data

Feb. 28, 1983 [JP] Japan .................................. 58-30903

[51] Int. Cl.³ .......................... G01N 1/28; A65C 9/08
[52] U.S. Cl. ..................................... 156/351; 156/57; 156/357; 156/363; 156/364; 156/556
[58] Field of Search ............... 156/556, 521, 522, 350, 156/351, 356–357, 358, 363, 362, 364, 57

[56] References Cited

U.S. PATENT DOCUMENTS 3,480,504 11/1969 Good et al. ........................ 156/356
4,033,809 7/1977 Tipton .............................. 156/57 X
4,120,991 10/1978 Ornstein et al. ................... 156/57 X
4,190,472 2/1980 Slonicki ......................... 156/357 X
4,203,797 5/1980 Stormby .............................. 156/521
4,455,188 6/1984 Stormby .......................... 156/357 X Primary Examiner—David Simmons
Attorney, Agent, or Firm—Sughrue, Mion, Zinn, Macpeak, and Seas

[57] ABSTRACT

An automatic specimen sealing system which provides totally automated sealing of glass slides. Slides are ejected sequentially at predetermined intervals onto a conveyor at a predetermined orientation. The size of the specimens held on the slides is detected, and liquid adhesive is supplied onto the slides in an amount determined in accordance with the thus-detected specimen sizes. Glass covers are then placed over the specimens, with the size of the glass covers being also selected in accordance with the specimen size. The slides with the covers placed thereon are next fed to a binding device where the covers and slides are bound together. Finally, the slides are assembled in trays.

2 Claims, 43 Drawing Figures

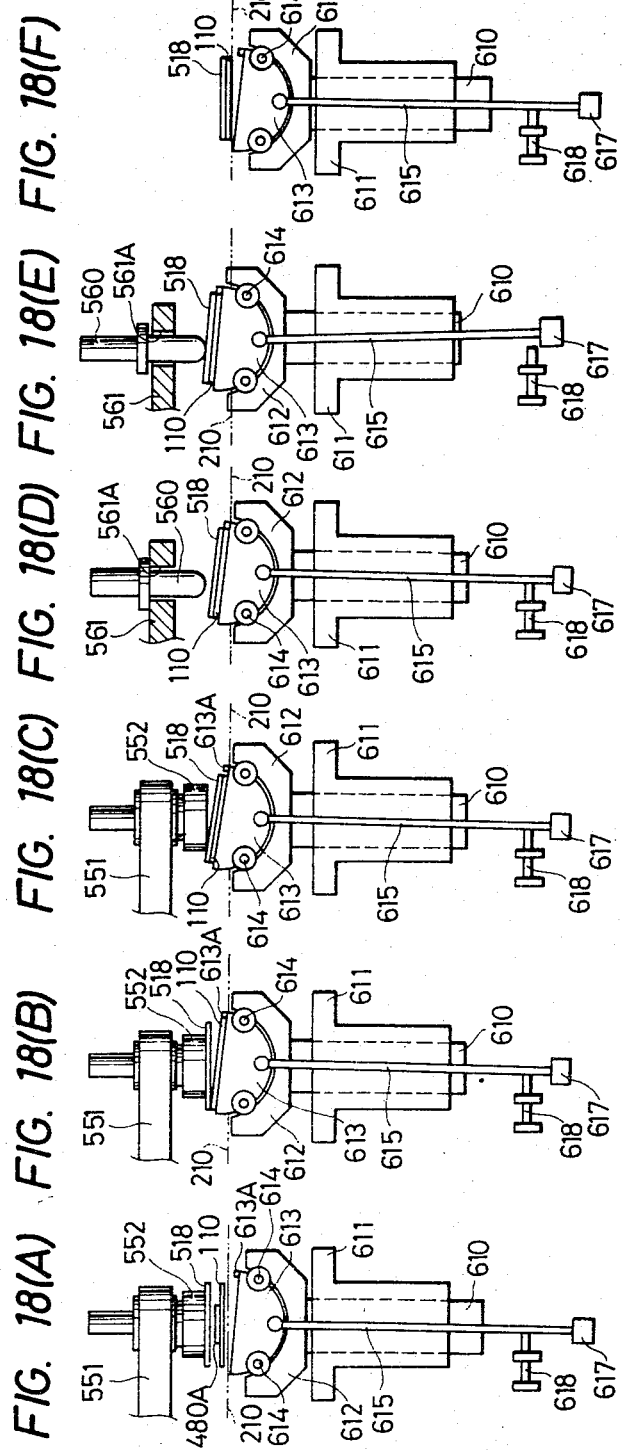

AUTOMATIC SPECIMEN SEALING SYSTEM

BACKGROUND OF THE INVENTION

This invention relates to an automatic specimen sealing system and, particularly, to an automatic specimen sealing system for performing automatically and continuously a series of operations of the type in which a glass slide having a thin specimen smeared thereon is conveyed along a conveyor and a binding liquid is applied and a glass cover is supplied to seal the specimen.

Generally, a tissue specimen for microscope examination that will be used for pathology or medical examination of cells is prepared through the steps of dehydrating a tissue sample by means of alcohol or the like, packing the sample with paraffin or the like, smearing a thin slice of the paraffin-packed sample on a glass slide, and subjecting the slide to a staining process. The slide is then stored in a cage and preserved in xylene or the like.

Then, the thus-preprocessed specimen is sealed by a cover of about 0.09 to 1.0 mm in thickness by the use of a binding agent. The specimen can be stored at this stage.

In the course of preparing the specimen, it is necessary to prevent destruction of the tissue and mixing of air therewith. Further, these operations must be done quickly; however, they were performed manually for the most part in the prior art.

In recent years, the respective processing steps have been automated individually, but the overall specimen sealing device was not fully automated. One such device has been developed by Schandon Southern Products Limited and is disclosed in Japanese Published Patent Application No. 109377/78. According to this disclosure, onto a glass cover with a binding liquid dropped thereon, a glass slide having a lower face onto which a sliced specimen has been placed is guided and the glass cover is pushed up against the slide positioned above the former to diffuse the binding liquid between the slide and the cover, whereby the specimen is sealed between the two glass members.

However, in this automatic specimen sealing device, the binding liquid is not applied directly to the specimen and will penetrate the specimen only after the cover has come into contact with the slide, thus the binding liquid may not penetrate sufficiently, resulting in voids.

Further, this prior art device can use only expensive glass covers of a standardized size. It is desirable to use glass covers, the size of which is selectable among several sizes according to the size of the specimens for economical reason.

Moreover, in this prior art device including a slide setting case for storing a stack of glass slides therein, an uppermost slide of the stack is grasped at its periphery by a fork provided at an end of a rotatable arm and the slide is carried to above a sealing position by rotation of the arm sequentially.

Thus, in loading the slides in the setting case, it is necessary to take out the slides stored in a container filled with xylol liquid one after another and to pile them up in the setting case. This operation is troublesome and a complicated slide pick-up mechanism is required for the device.

SUMMARY OF THE INVENTION

In view of the foregoing drawbacks, it is an object of the invention to provide a automatic specimen sealing system which operates in such a manner that, after the glass slides are simply loaded in a supply device, a liquid adhesive and a glass cover in an amount and size corresponding to the size of a specimen are automatically supplied onto the slide and the specimen is sealed thereby, whereby mixing of air is prevented and specimens of a high quality are obtained.

In summary, the invention resides in an automatic specimen sealing system comprising a glass slide supply device for passing down slidingly the glass slide one after another at a certain time interval to a predetermined position on a conveyor oriented at a certain attitude, a conveyor device for conveying the slide supplied on the conveyor at a predetermined interval, a discrimination device for detecting optically the size of a specimen on the slide being conveyed on the conveyor, a pouring device for supplying a liquid adhesive onto the glass slide in an amount appropriate to the size of the specimen, a glass cover sorting/supplying device for selecting glass covers of a size determined by the size of the specimen and supplying the selected glass cover onto the glass slide conveyed to a supply position on the conveyor, a binding device for lifting up the glass slide from the supply position to perform sealing of the specimen between the slide and the glass cover and then return the glass slide together with the glass cover to the supply position, a storage device for moving in parallel a certain number of glass slides returned to the supply position and moved by the conveyor device into a tray, and a control unit for effecting in synchronization with the conveyor device the respective processing of the glass slide supply device, the discrimination device, the pouring device, the glass cover sorting/supplying device, and the binding device.

BRIEF DESCRIPTION OF THE DRAWINGS

FIGS. 18(A) through 18(F) are explanatory views showing step by step a series of binding operations of the binding device;

DESCRIPTION OF THE PREFERRED EMBODIMENTS

A preferred embodiment of the invention will be described with reference to the drawings.

Figure 1:
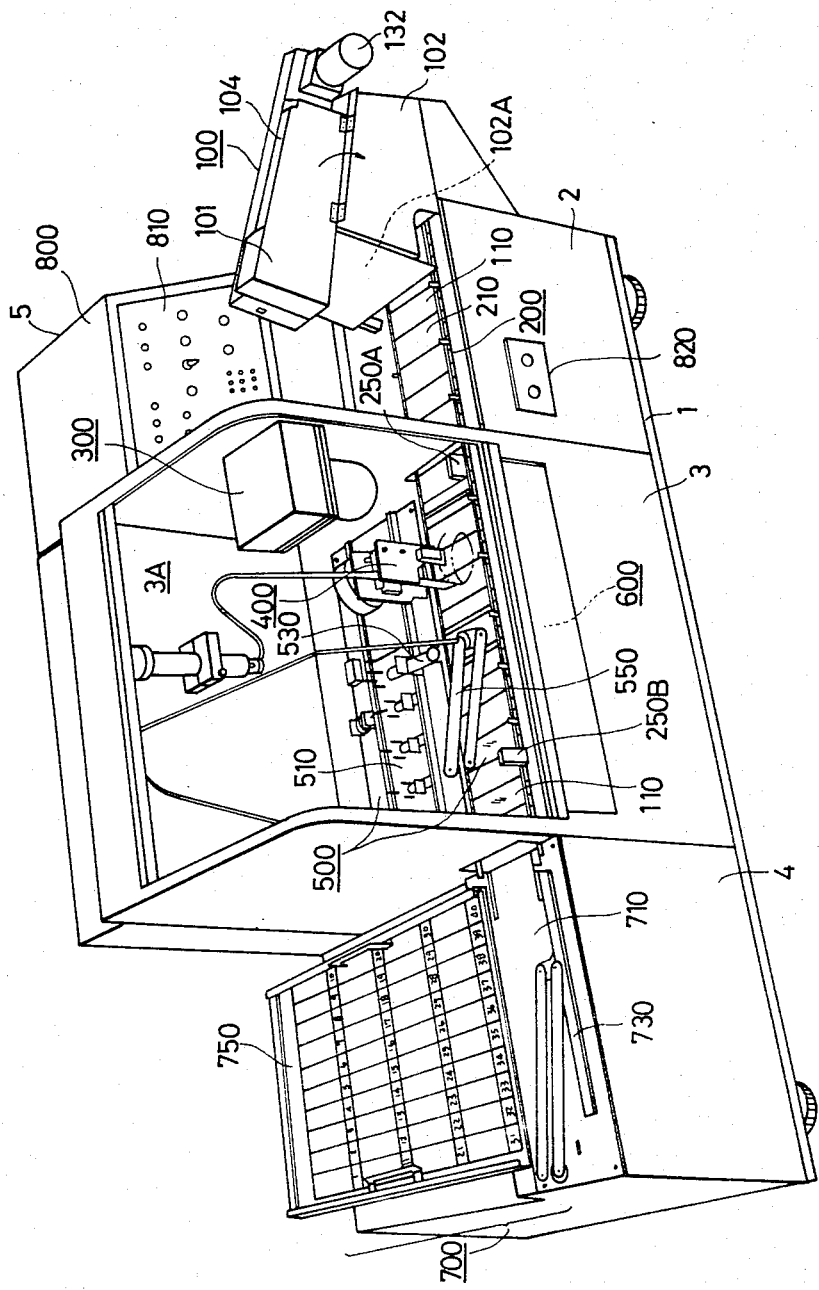
FIG. 1 is a perspective view showing an example of an automatic specimen sealing system according to this invention.

FIG. 1 shows a preferred embodiment of an automatic specimen sealing system constructed according to the invention. First, units which form the principal elements of the present system and the operations thereamong will be described in brief with reference to FIG. 1. In FIG. 1, 1 is a base plate, 2 is a glass slide supply unit, 3 is a sealing unit, 4 is a tray unit, and 5 is a control unit. In addition, for the sealing unit 3, a transparent dust-blocking cover 3A is provided for observation of sealing operations.

Further, reference numeral 100 is a glass slide supply device of the unit 2, 200 is a conveyor device for moving at a present interval glass slides 110 which are supplied from the glass slide supply device 100. Thus, the glass slide 110 supplied onto a conveyor 210 is conveyed from right to left (in the drawing), during which time at first the size of a specimen (not shown) is detected by a discrimination device 300 in the sealing unit 3. Then, the glass slide 110 is guided to a position below an adhesive supply device 400 where a liquid adhesive is supplied onto the glass slide 110 from the adhesive supply device 400 in response to the specimen's size detected by the specimen detection device 300.

Reference numeral 500 is a glass cover sorting supplying device. In this stage, a glass cover whose size corresponds to the size of the specimen detected by the detection device 300 is selected and supplied; accordingly, the glass slide 110 having the liquid adhesive is supplied with the glass cover whose size is large enough to cover and seal the specimen. That is, in the glass cover sorting supplying device 500, a glass cover of approximate size is automatically picked up from a glass cover sorting/holding device 510 by an extracting mechanism 550 and, in turn, the selected cover is guided by a transferring mechanism 550 to a position above the glass slide 110 on which the liquid adhesive is deposited.

Below the glass slide 110 at the binding station there is provided a sealing device 600 which performs binding of the glass slide 110 with the glass cover through up-down movement at an appropriate timing. At this station, the glass slide 110 is shifted onto a receiving table (not shown) of the sealing device 600 and the glass cover is allowed to full down lightly on the former and a small pushing force is applied to the glass cover, whereby binding and sealing are completed.

The sealed slides are pushed forward one after another to a slide assembly area 710 of a housing device 700. Then, when a certain number (ten, in this example) of sealed glass slides 110 have been accumulated in the slide assembly area 710, they are pushed toward a tray 750 by a pushing mechanism 730. When a total of 40 slides have been received in the tray, the preparation of one gang of sealed glass slide is completed.

In addition, 800 is a control device for controlling a series of such sealing operations by the use of a microcomputer, and 810 is a console panel therefor. The console panel is provided with indicators, switches, and indicating devices for presenting several indications upon occurrence of fault conditions, whereby the specimen sealing device can be controlled and its operations monitored through the console panel 810. Further, 820 is a switch box including switches for starting and stopping the specimen sealing device.

The principal units of which the automatic specimen sealing system of the invention is composed will now be described in more detail.

Figure 2:
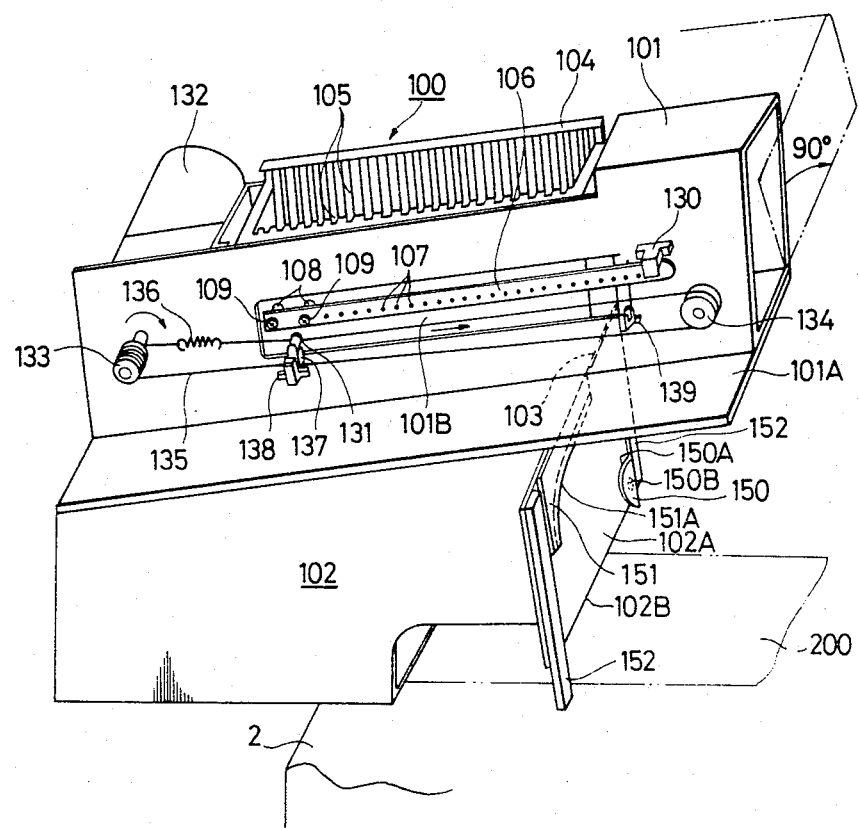
FIG. 2 is a perspective view showing an example of a glass slide supplying device.

FIG. 2 shows an example of the glass slide supply device 100. The conveyor device 200 onto which the glass slides 110 are placed is illustrated in the lower portion of the drawing.

A glass slide holder 101, together with its bottom plate 101A, is secured on a holder support 102 with an inclination. The support 102 is mounted on the glass slide supply unit 2 above the conveyor device 200. Further, the bottom plate 101A is formed with a slit 103 for allowing the glass slide 110 pass along a sliding surface 102A positioned below by force of gravity. 104 is a slider reciprocatable along an inner face of the holder 101. The upper portion of the slider 104 is normally left open. Inside the slider 104 there are formed a certain number of, for example, 40, vertical grooves 105 with a regular pitch which may receive a total of 40 glass slides 110 that correspond to the glass slides to be received in two cages for staining tissues, which are available in the market, so that the 40 glass slides out of two cages each containing 20 slides may be transferred into the grooves at a time. Thus, the glass slides 110 can be transferred and loaded directly from the staining cage into the slider 104 with the lengthwise direction of the glass slides being aligned with that of the grooves 105.

FIG. 2 illustrates the positional relationship between the slider 104 and the holder 101 with the glass slides 110 loaded therein. In this position, the bottom of the slider 104 is out of place relative to the slit 103 so that the glass slide 110 does not fall from the slider 104. Further, the holder 101 is pivotable 90 degrees rearwardly in the drawing. Thus, loading of the glass slides 110 may be performed while the holder 101 is in such a position.

Reference numeral 106 designates a gauge plate having detection holes 107 formed at intervals equal to the loading spacing for the glass slide 110. To fix the gauge plate 106 on the side face of the slider 104, screws 109 with shafts 108 are provided so that the gauge plate 106 is held parallel to the holder 101 projecting outwardly from a slide slot 101B of the holder 101.

Reference numeral 130 is a photosensor used to detect the position of the detection holes 107. With this photosensor, the slider 104 is shifted at a pitch corresponding to the loading spacing of the glass slide 110. 131 is a working shaft projecting outwardly beyond the side plate of the holder 101 from the slider 104, 132 is a motor having a reduction gear and used to operate the slider 104, 133 is a driving screw pulley directly coupled to the motor 132, 134 is a guide pulley, 135 is an endless wire passing over the working shaft 131 and pulleys 133 and 134 to operate the slider 104 by means of the motor 132.

In order to hold the wire 135 a spring 136 is interposed. Further, to an end of the working shaft 131 is attached a shield plate 137 for the sensor.

138 and 139 are a start-position detection sensor and a supply-termination-position detection sensor, respectively, attached to the side face of the holder 101. The sensors 138 and 139 are implemented with photosensors, for example, and are provided with grooves through which the shield plate 137 can pass. When the working shaft 131 is at the position of the sensor 138, it can detect that the slider box 104 is positioned at the supply start position or, when the working shaft 131 is at the position of the sensor 139, it can detect that the slider box 104 is positioned at the supply termination position, whereby corresponding signals are supplied to the control unit 800 shown in FIG. 1.

Figure 3:
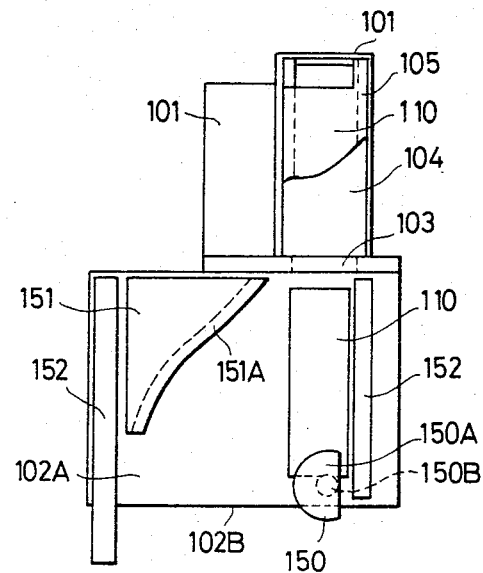
FIG. 3 is a front view of the glass slide supplying device and a sliding surface thereof.

Next, the sliding surface 102A of the holder support 102 will be described. As shown in FIG. 3, the sliding surface 102A is provided with guide members 150, 151 and 152. The guide member 150 is composed of a shaft portion 150B and a flange portion 150A, and may be made of a material having some elasticity such as plastics, which material is desirable for handling fragile members such as glass plates. Further, the guide member 151 is also formed with a guide flange 151A. 152 are guide members disposed on either side of the sliding surface 102A.

As a glass slide 110 slides down from the slider 104 along the thus-constructed sliding surface 102A, the lower end portion of the glass slide 110 fits first into the groove formed between the flange 150A of the member 150 and the sliding surface 102A and abuts upon the shaft portion 150B. In this state, the lower end of the glass slide 110 is supported by the shaft portion 150B at a point a little rightward from the center as viewed in FIG. 3. Because this position is unstable, the glass slide 110 rotates in the counterclockwise direction about the shaft portion 150B and, while being supported by the grooved between the flanges 150A and 151A and the surface 102A, it slides downwardly sideways.

Figure 4:
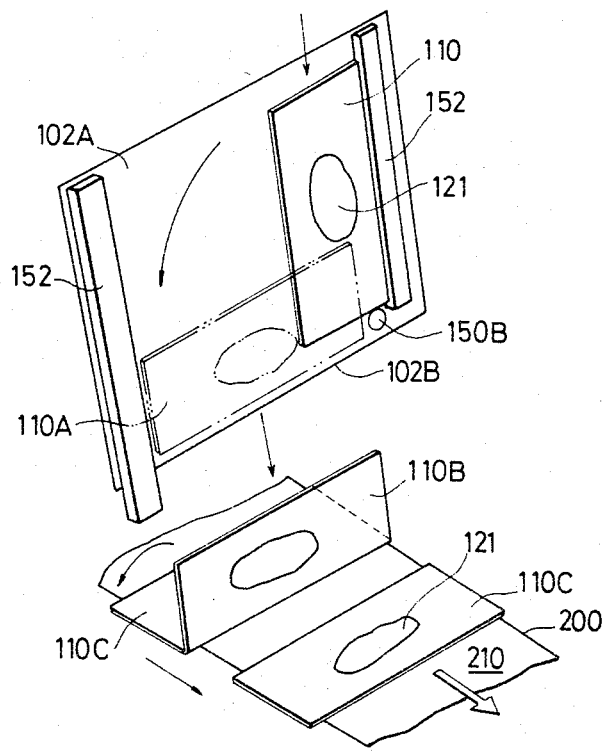
FIG. 4 is a perspective view showing the movement of the glass slide along the sliding surface and onto a conveyor.

Here, the sliding surface 102A is inclined as to mate with the inclination of the groove 105. Thus, when the glass slide 110A comes below the lower margin 102B of the sliding surface 102A and assumes a position 110B shown in FIG. 4, the slide has an inclination similar to that of the sliding surface 102A on account of the inertia at the time of its falling movement. Then, upon the landing of a longer side of the glass slide 110 on the conveyor 200, the glass slide drops down immediately, increasing its inclination and, finally, assuming the flat position designated at 110C. In this drawing, the thick arrow indicates the direction of the glass slide 110C being conveyed, and 121 designates the specimen smeared on the glass slide 110.

Next, the operation of the thus-constructed glass slide supply device 100 will be described. As described above, the holder can be rotated by 90° as shown by dashed lines in FIG. 2. Thus, in loading the glass slides 110, the holder 101 is rotated to the position indicated by dashed lines in FIG. 2. The vertical grooves of the slider box 104 are aligned in pitch with the glasses in the staining cage (not shown), and then the glass slides 110 are allowed to slide from the cage into the slider 104.

Figure 5A:
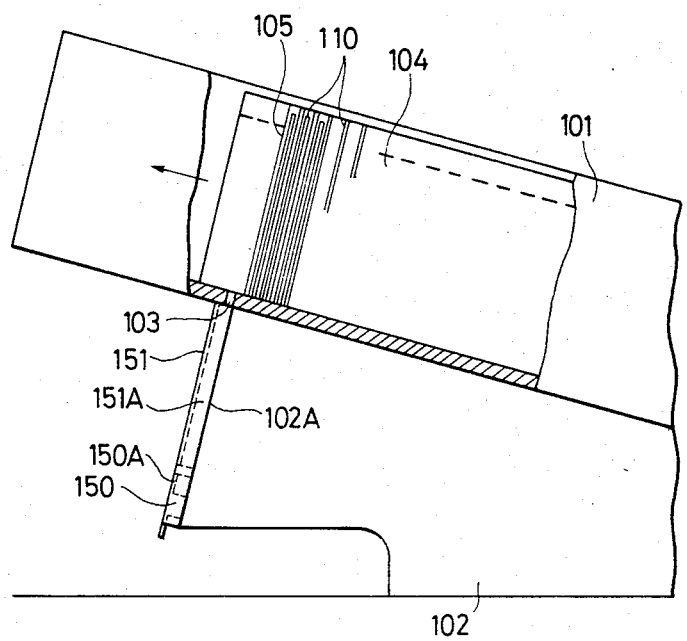
FIGS. 5(A) and 5(B) are a side view and a top view, respectively, of the glass slide supplying device, partially cut away.
Figure 5B:
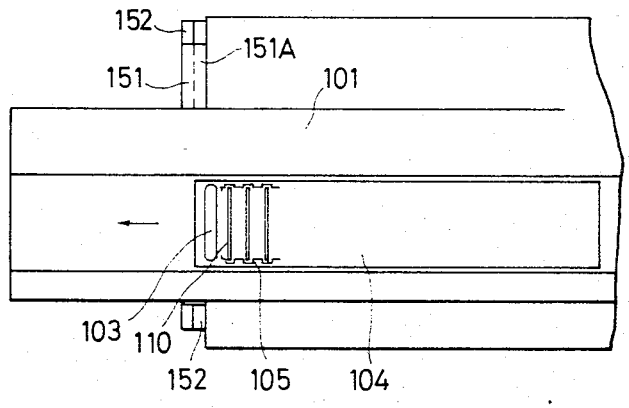

Here, it should be noted that the loading of the slides is performed so that the face of the slide on which the specimen has been smeared is on the upper side of the inclined slide 110. After the loaded holder 101 is returned to the initial position, the sealing start button is pushed to actuate the control unit 800, whereby a series of automatic sealing operations is commenced. At such time, the slider 104 is held in the state as shown in FIG. 2. That is, the relative positions of the slider 104 and the holder support 102 below the former are as shown in FIGS. 5(A) and 5(B). Upon pushing the start button 820 (see FIG. 1), the motor 132 is energized, whereby the stainless endless wire 135 moves the slide 104 rightwardly (as viewed in FIG. 2) through the working shaft 131.

It should be noted that the mechanism for driving the wire 135 includes a slip mechanism (not shown). Thus, in case the movement of the slider 104 is abnormal, a slipping action is introduced so that the device and the glass slide are prevented from being damaged.

As the slider moves a distance corresponding to one spacing between two adjacent glass slides, the detection hole 107 in the gauge plate 106 with the same spacing is detected by the sensor 130. The resulting detected detection signal is supplied to the control device 800, which in turn supplies a signal to stop the motor 132. In the stopped position of the slider 104, the first groove 105 is positioned directly above the slit 103. Accordingly, the glass slide 110 received in this groove 105 is allowed to slide down through the slit 103 and along the sliding surface 102A below the former.

The falling glass slide 110 is once received by the groove between the flange 150A of the guide member 150 and the surface 102A, then it is guided by the guide members 150, 151 and 152 and supplied to the conveyor device 200 positioned below as described hereinabove.

After the stop time corresponding to the time required to perform the succeeding processes has elapsed, the motor 132 is again energized to shift the slider 104 one spacing, whereupon the next glass slide 110 is supplied to the conveyor device 200. These operations are repeated. In response to such repetitive operations, the slider 104 is shifted rightwardly as viewed in FIG. 2, and correspondingly the working shaft 131 mounted on the slider 104 is also shifted. When the working shaft 131 reaches the position of the sensor 139, the presence of the shield plate 137 mounted on the working shaft 131 is detected by the photosensor 139 indicating the completion of supply of the slides. Thus, a signal to stop the motor 132 is generated.

After the completion of a series of sealing operation by the sealing device, the motor 132 is energized to return the slider 104 to the initial position shown in FIG. 2.

Next, the conveyor device 200 will be described.

Figure 6A:
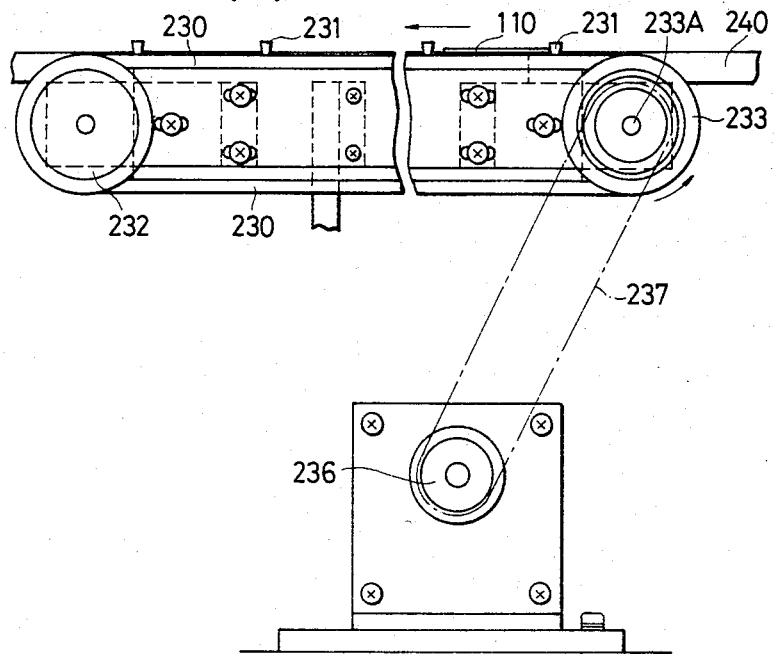
FIGS. 6(A) and 6(B) are a side view and a partially sectional view, respectively, of a conveyor device employed in the automatic specimen sealing system of the invention.
Figure 6B:
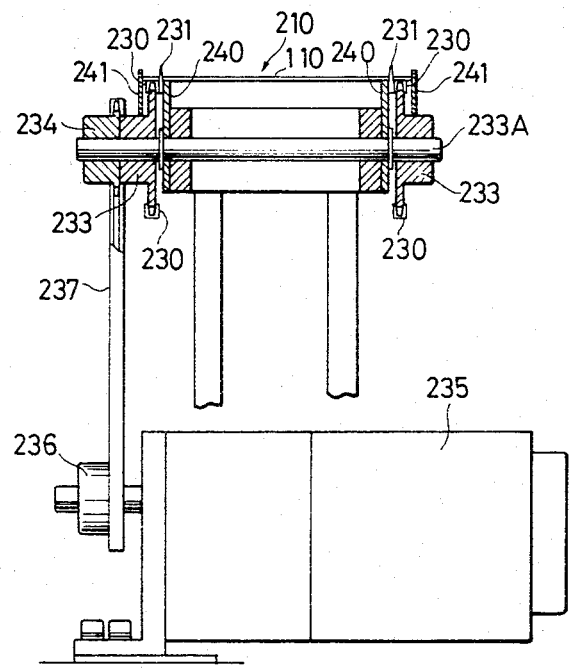

FIGS. 6(A) and 6(B) illustrate schematically the conveyor device 200. As shown in FIG. 1 the conveyor device 200 includes a conveyor 210 extending from a position below the holder support 102 to the inlet of the slide assembly area 710 above the storage unit 4. Glass slides 110 supplied from the holder 100 onto the conveyor 210 are subjected to repetitive shifting and stopping by the conveyor device 200, moving in stages, during which the several manipulations necessary for sealing are performed.

Reference numeral 230 is a roller chain, 231 are feed claws mounted on the roller chain at intervals. The roller chain 230 is engaged between sprockets 232 and 233, a driven sprocket 234 is attached to a sprocket shaft 233A, a driving sprocket 236 is attached to a control motor 235, and a roller chain 237 is engaged between the latter two sprockets. Accordingly, by energizing the motor 235, the sprocket 233 is rotated in the counterclockwise direction as viewed in FIG. 6(A), whereby the roller chain 230 is moved from right to left.

240 are rails laid so as to mate with the conveyor 210. 241 are guide plates mounted in parallel along a short margin of the glass slide 110 on both sides. The glass slide 110 is supported slidably by the upper face of the rails 240 and restrained by both guide plates 241 from moving laterally off the conveyor 210. It is preferably that the rails 240 and guide plates 241 be smooth, made, for example, of a plastics material. Further, the rails 240 are designed so that their upper faces are higher than the upper face of the roller chain 230. Accordingly, the glass slide 110 is held between the claws 231 on the rails 240 and shifted on the rails 240, in response to movement of the roller chain 230, by the feed claws 231 without contacting with the roller chain 230.

The drive mechanism of the roller chain 230 includes a slip mechanism (not shown). Thus, in case the conveyor device 200 is subjected to an abnormal force, slipping takes place, whereby damage to the device, glass slides and the like is prevented.

The repetitive operation of shifting and stopping of the thus-constructed conveyor device 200 is done under the control of the control device 800. These operation will be described below in connection with the control device 800.

Figure 7:
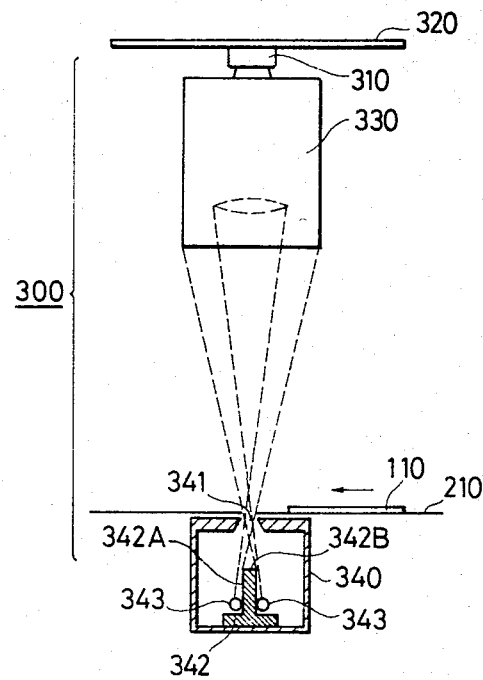
FIG. 7 is a schematic view showing a discrimination device of the automatic specimen sealing system of the invention.

Next, the structure of the detection device 300 will be explained. FIG. 7 shows schematically the detection device 300, in which 310 is a sensor array having a plurality of photosensors mounted thereon, and 320 is a printed circuit board to which a group of sensors are connected.

The sensor array 310 and printed circuit board 320 and a lens assembly 330 including a plurality of lenses are disposed above the conveyor device 200 facing the conveyor 210 below. 340 is a light projector mounted underside the conveyor 210. The projector 340 has on the side contacting the conveyor 210 a slit 341. On the bottom position of the projection 340 just under the slit 341 there are provided a shield member 342 with a vertical plate 342A and incandescent lamps 343 located at both sides of the vertical plate 342A.

An upper face 342B of the vertical plate 342A facing the slit 341 is colored black so that it does not reflect light and provides a black background to the lens assembly 330 through the slit 341, excluding direct light from the lamps 343. That is, as shown by broken lines in the drawing, light projected upward directly from each lamps 343 is restricted by the shield member 342 and the slit 341, and is not received by a group of sensors in the sensor array 310 through the lens assembly 330.

Figure 8:
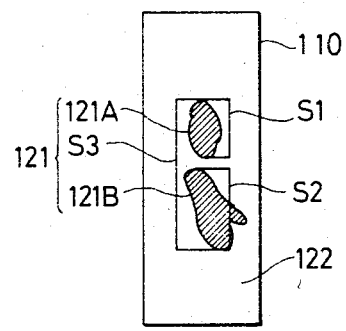
FIG. 8 is an explanatory view showing examples of the glass slide and a specimen.

Thus, when the glass slide 110 is conveyed along the conveyor 210, if there is no specimen on the slide, none of the sensors in the sensor array 310 receive and detect light because of the transparency of the glass. To the contrary, if a specimen, such as indicated by 121A and 121B with lengths 51 and 52 in the lengthwise direction of the glass slide, is present on the glass slide 110 as shown in FIG. 8, as the glass slide 110 passes the slit 341, the light is scattered thereby. Scattered light is thus detected by some of the sensors of the sensor array 310, and accordingly the total length S3 of the specimens 121A and 121B is detected. The detected length S3 is compared with a plurality of preselected lengths and a discrimination signal corresponding to the selected length is provided through the control unit hereinafter described.

Some slides 110 may have at an end thereof a frosted portion 122 to facilitate numbering and/or marking thereof (see FIG. 8). In that case, the scattered light can be received by the sensor array 310 each time the glass slide 110 passes over the slit 341.

Figure 9:
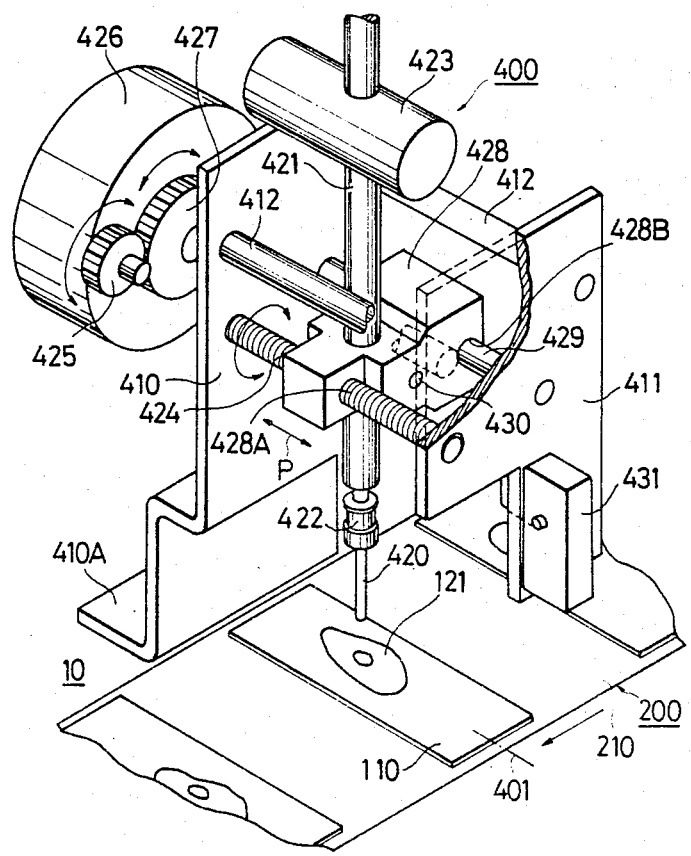
FIG. 9 is a perspective view showing the structure of a pouring device of the automatic specimen sealing system of the invention.

Next, the pouring device 400 for dropping the liquid adhesive onto the glass slide 110 will be described with reference to FIG. 9. In this drawing, 410 and 411 are support frames for the adhesive supply device 400 placed on both sides of the conveyor 210. The support frames 410 and 411 are mutually connected by connection rods 412, and a flange portion 410A of the support frame 410 is secured on a base body 10.

420 is a nozzle used to jet the liquid adhesive, 421 is a liquid adhesive supply tube, and the nozzle 420 and the supply tube 421 are connected by a connection member 422. Further, 423 is a control valve for controlling the supply of the liquid adhesive. By this control valve 423 a switching time to supply the liquid adhesive is controlled, and thereby the amount of supplied liquid can be changed. Because the liquid adhesive is pressurized by a device hereinafter described, it is possible to regulate the liquid amount being supplied in proportion to the valve open time of the valve 423.

424 is a lead screw supported by the support frames 410 and 411. To the lead screw 424 is connected a gear 425. The gear 425 meshes with a large gear 427 coupled to a stepping motor 426 and is driven by the latter to rotate the lead screw 424. 428 is a nozzle holder used to support the supply tube 421 as well as the nozzle 420. The nozzle holder 428 is engaged with the lead screw 424 through a screw hole 428A. Through a guide hole 428B passes a guide rod 429, whereby the nozzle holder 428 is movably supported (as indicated by the arrow P in the drawing) by the guide rod 429 and the lead screw 424 while holding the nozzle 420 in the downward position. A ball slide (not shown) or the like is provided between the guide rod 429 the guide hole 428B to ensure smooth movement.

430 is a hole for a screw to secure the supply tube 421 to the nozzle holder 428. A screw inserted in the screw hole 430 is provided to adjust the height of the nozzle 420 relative to the glass slide 110.

431 is a limit switch attached to the support frame 411. In the present device, the nozzle holder 428 is returned to the initial position each time the liquid adhesive is jetted to one glass slide 110. To assure the above, as the nozzle holder 428 moves rightwardly and comes into contact with the limit switch 431, the initial position of the nozzle holder 428 is confirmed and the holder 428 is stopped at the initial position to wait for a next jetting operation.

Figure 10:
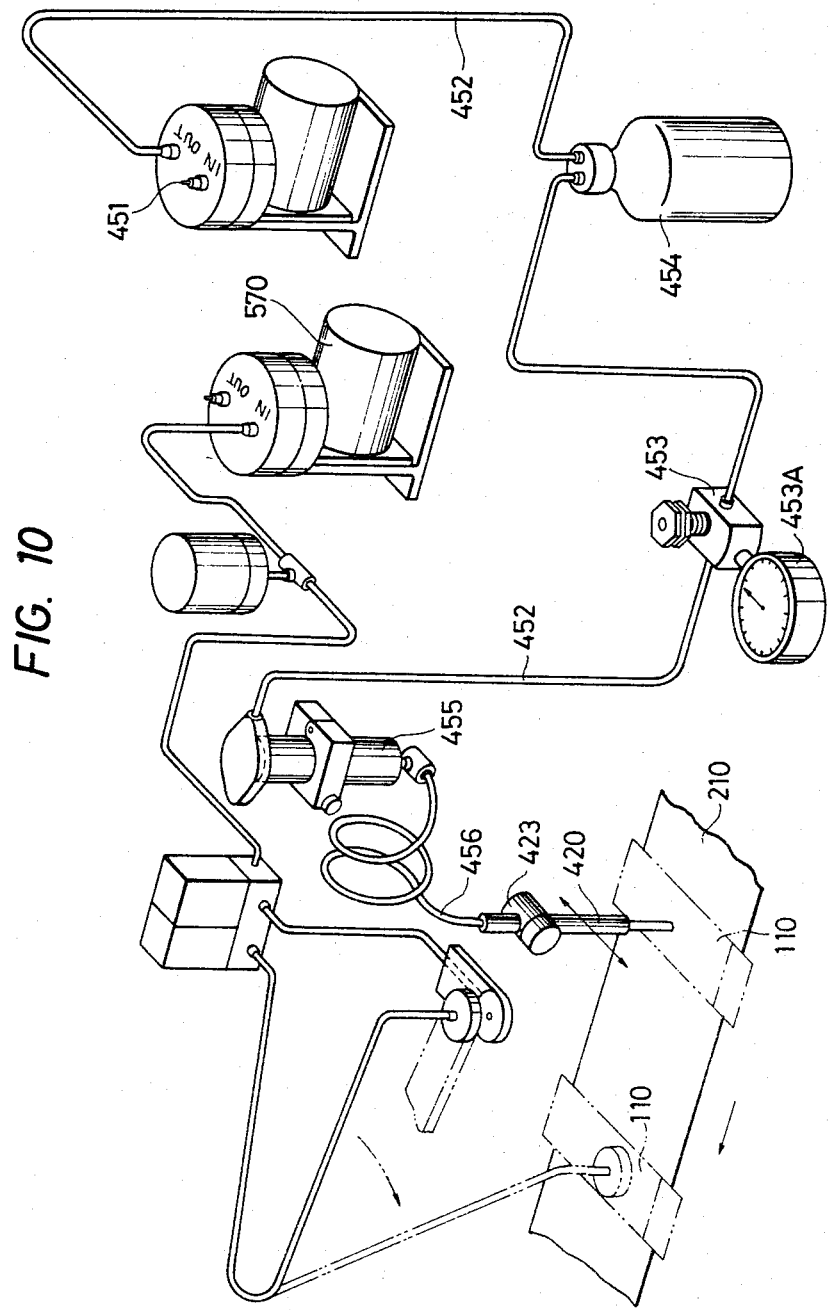
FIG. 10 is a perspective view showing an example of a liquid agent supply mechanism employed in the pouring device.

FIG. 10 shows an example of the pressurized liquid supply system for supplying a liquid of a certain pressure to the control valve 423. 451 is an air compression pump to pressurize air. The air pressurized by the pump 451 is conducted through a tube 452 and an air tank 454 to a pressure regulator 453 by which a certain pressure, for example, 0.1 kg/cm$^2$, is maintained. 453A is a pressure gauge.

455 is a pressurized tank filled with the liquid adhesive. The liquid adhesive is pressurized in the pressurizing tank 455 by means of the pressurized air from the pressure regulator 453 through the tube 452 and is supplied through a fluorine resin tube 456 to the control valve (electromagnetic control valve) 423. The switching (ON/OFF) time of the valve 423 is controlled whereby the liquid adhesive in a volume corresponding to the size of the specimen is jetted from the nozzle 420.

Figure 11:
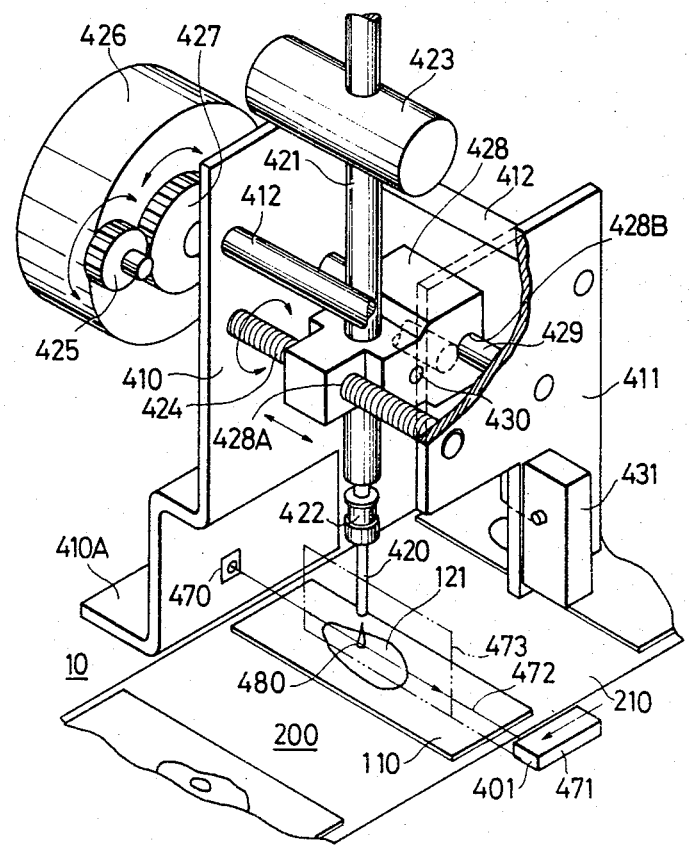
FIG. 11 is a perspective view showing the operation of the liquid supply mechanism and a liquid drop detecting mechanism.

FIG. 11 shows a jetting detection mechanism for the liquid adhesive, in which 470 and 471 are a light-emitting element and a light detecting element, respectively. 472 is a light beam travelling from the light-emitting element 470 toward the light-detecting element 471. The light-emitting element 470 and the light-detecting element 471 are so disposed that the light beam 472 travels in the same direction as the direction of movement of the nozzle 420, that is, orthogonal to the direction of movement of the conveyor and in a vertical plane 473 including the nozzle 420.

In the mechanism so arranged as above, the liquid 480 jetted from the nozzle 420 falls along the vertical plane, irrespective of the position of the nozzle 420, and interrupts the light beam 472, whereby execution of pouring can be detected. Visible red light is suitable for use in this application. It is desirable for the light beam 472 from the light-emitting element 470 to be as narrow as possible.

Next, the pouring operation by the thus constructed liquid projecting device will be described.

The control device 800 shown in FIG. 1 includes a memory device (not shown) in which are stored the presence/absence of the glass slides 110 at each shifted position each time the individual glass slides 110 move step by step along the conveyor 210. When the presence of a glass slide 110 conveyed to a pouring step position 401 by the conveyor device 200 is confirmed by the control device 800, the control unit supplies a signal to operate the stepping motor 426. Accordingly, the nozzle holder 428 is shifted leftwardly (as viewed in the drawing) from the initial position in response to rotation of the lead screw 424. The detection device 300 discriminates (senses) the size of the specimen 121 on the glass slide 110. On the basis of a detection signal thereby produced, the control device 800 determines the number of liquid projecting points. In response to the operation signal based on this determination, the stepping motor 426 is controlled so as to stop liquid supply, and afterwards, move further and stop.

Moreover, to the control valve 423 a pouring signal, based on the discrimination signal relating to the size of the specimen 121, is supplied each time stepping motor 426 is stopped. In the described embodiment, a pouring signal that results in four different pouring time intervals of the control valve 423 is employed.

After the control valve 423 dispenses liquid for a time interval corresponding to the pouring signal, a signal causing reverse rotation is applied to the stepping motor 426, whereby the holder 428 together with the nozzle 420 is returned to the initial position This return to the initial position is detected by the limit switch 431, and hence it is possible to stop the motor 426 thereby to stop the holder 428 at the initial position. During this operation, whether the liquid has been dispensed or not is detected by the liquid detection mechanism. Specifically, in case the liquid is at plural pouring points, each jetting operation is detected. Accordingly, when no jetting operation has been executed, a no-jetting signal is applied from the detection mechanism to the control device 800. Then, the control device 800 immediately issues a warning, such as an audible alarm.

Figure 12:
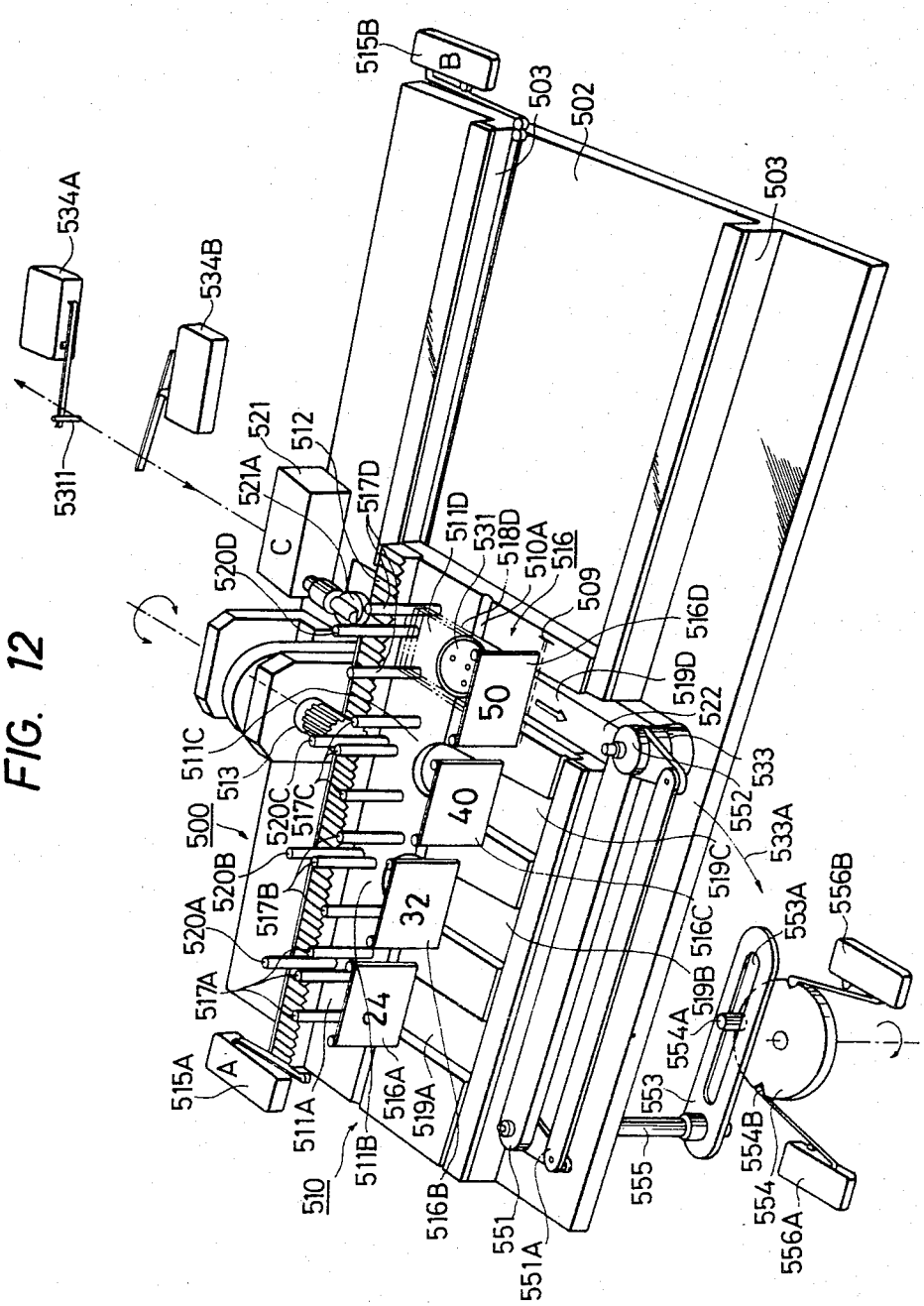
FIG. 12 is a perspective view showing the structure of a glass cover sorting/supplying device of the automatic specimen sealing system of the invention.
Figure 13:
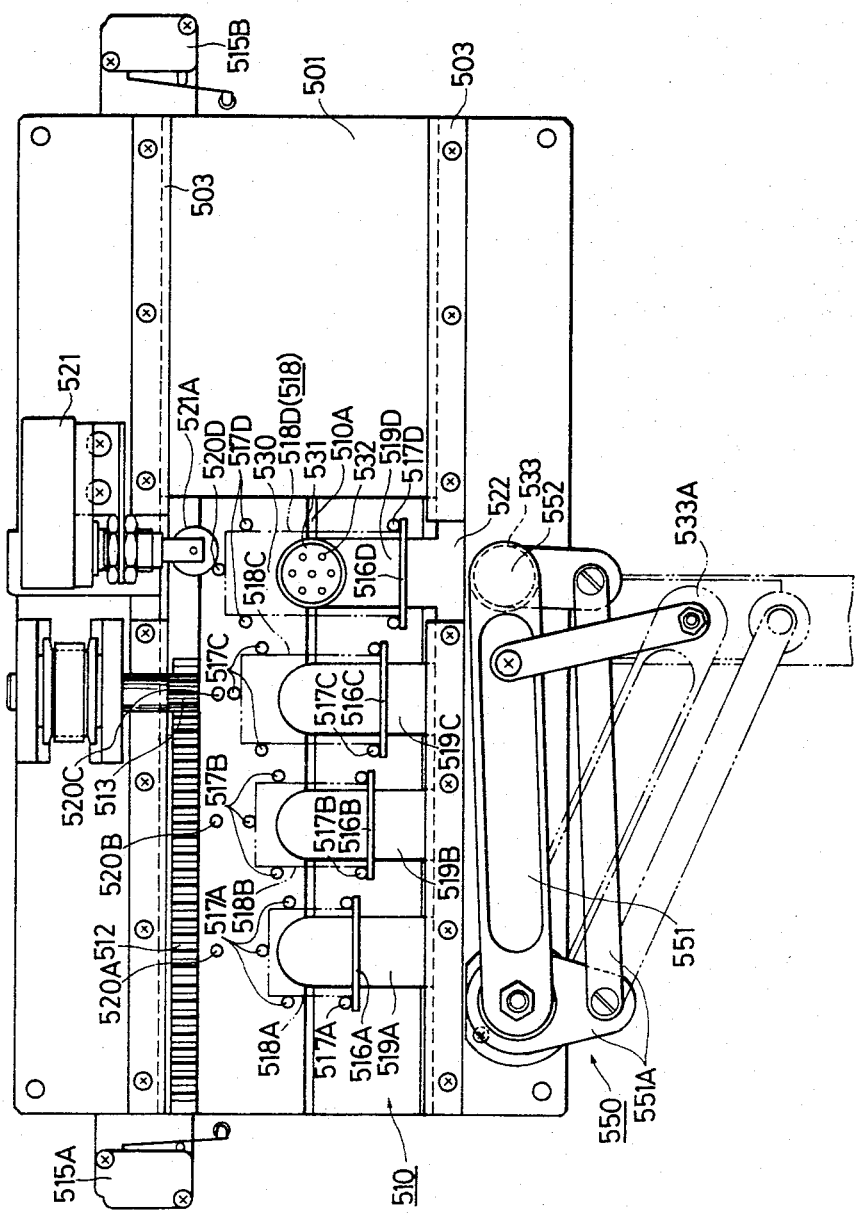
FIG. 13 is a plane view corresponding to FIG. 12.

Next, the cover glass sorting/supplying device 500 will be described with reference to FIGS. 12 and 13. In the drawings, 502 is a base plate of the cover glass sorting/supplying device 500. A sorter 510 is reciprocatably supported by rails 503 mounted on the base plate 502. It is noted that the rails 503 are parallel to the conveyor device 200. 512 is a rack formed on the upper face of the sorter 510. 513 is a pinion gear operated by a drive motor (not shown in this drawing). The sorter 510 is moved reciprocatingly by the motor through the pinion gear 513 and rack 512.

515A and 515B are a start point limit switch and an end point limit switch, respectively, provided in the vicinity of the ends of the rack 512. When either end of the sorter 510 comes into contact with the limit switch 515A or 515B, it is detected that the sorter 510 is present at the start point or at the end point, whereby the motor is stopped. 516A, 516B, 516C and 516D are flash boards. Four kinds of cover glasses of diameters 24 mm, 32 mm, 40 mm and 50 mm, for instance, are stored in stacks in areas 511A, 511B, 511C and 511D defined by the flash boards 516A, 516B, 516C and 516D and pins 517A, 517B, 517C and 517D provided on the rear sides thereof. In FIG. 13, 518A, 518B, 518C and 518D designate the stored respective cover groups. 510A is a groove which is formed to provide easy removal of the glass covers 518 from the front of the sorter 510.

Further, in the portions of the sorter 510 facing the respective front ends of the areas 511A, 511B, 511C and 511D storing the respectively differently sized glass covers 518A, 518B, 518C and 518D therein, there are formed parallel grooves 519A, 519B, 519C and 519D of the same shape. Between the lower faces of respective flash boards 516A, 516B, 516C and 516D and the upper face of the sorter 510, gaps 509 are provided through which only the lowermost ones of the glass covers 515A or 518D can pass. 520A, 520B, 520C and 520D are position detection pins positioned in the vicinity of the rack 512 and outside the corresponding areas 511A to 511D and aligned with the center lines of corresponding parallel grooves 519A, 519B, 519C and the 519D. 521 is a selection switch including a limit switch operated when any of the areas 511A to 511D is selected.

The selection switch 521 is operated by means of the position detection pins 520A through 520D when the motor is energized by the selection signal to select, on the basis of the determination made by the detection device 300, a glass cover 518 suitable for the specimen on the glass slide 110 being conveyed. That is, in the course or movement of the sorter 510 (which is driven by the motor from the start position detected by the limit switch 515A), the selection switch 521 is operated when the contact roller 521A of the selection switch 521 comes into contact with the position detection pins 520A through 520D in the order of pins 520D, 520C, 520B, and 520A. Therefore, from the number of times of operation of the selection switch 521, the position of any of the areas 511A to 511D can be detected. Thus, when the contact roller 521A of the selection switch 521 comes into contact with the position detection pin 520 corresponding to the area where the selected glass cover 518 is stored, the motor is deenergized to bring the sorter 510 to a stop.

522 is an extraction port formed by cutting away a portion of the rail 503 on the front side. In the described embodiment, the sorter 510 is stopped at the position where the glass cover 518D can be extracted. 531 is a suction disc of the extraction mechanism 530 used to extract the glass cover 518 when the sorter 510 is in the stopped state. The suction disc 531 has plural suction holes 532. Thus, when the sorter 510 comes to a stop, the lowermost one of the glass covers 518 stored in the pile is attracted with the use of the suction holes 332 and a vacuum pump (not shown).

Further, the suction disc 531 has an arm (not shown) by which the suction disc 531 can be moved along the parallel grooves 519 (519D in the embodiment shown) and can be projected to a transfer position 533 outside the rail 503. 534A and 534B are limit switches actuated by a pin 5311 connected to the arm and used to position the suction disc 531 at the suction-attraction position and also at the transfer position 533. 551 is an arm of a transfer mechanism 550 which has at its end a suction disc 552 used for transfer. Together with a link member 551A, the arm 551 is composed of a pantograph mechanism which is rotatable at one of its joints about a rotary shaft 555 from the illustrated position to a supply position 533A in the clockwise direction without changing the attitude of the glass cover received at the transfer position 533. 553 is an arm attached to the rotary shaft 555 having a slide groove 553A into which a pin 554A of a rotary plate 554 is slidably fitted. The rotary plate is rotated by a motor (not shown). The rotary plate 554 is provided with a notch 554B around its periphery. 556A and 556B are limit switches used for transfer. For example, if the rotary plate 554 is rotated in the clockwise direction when the notch 554B 551 and the suction disc 552 are moved to the transfer position 533 where the motor is stopped for a certain time and then again energized. Then, when the notch 554B comes to the position of the limit switch 556B and the arm 551 is at the supply position 533A, the motor is stopped for a certain time and again energized in the same manner as described above.

Figure 14:
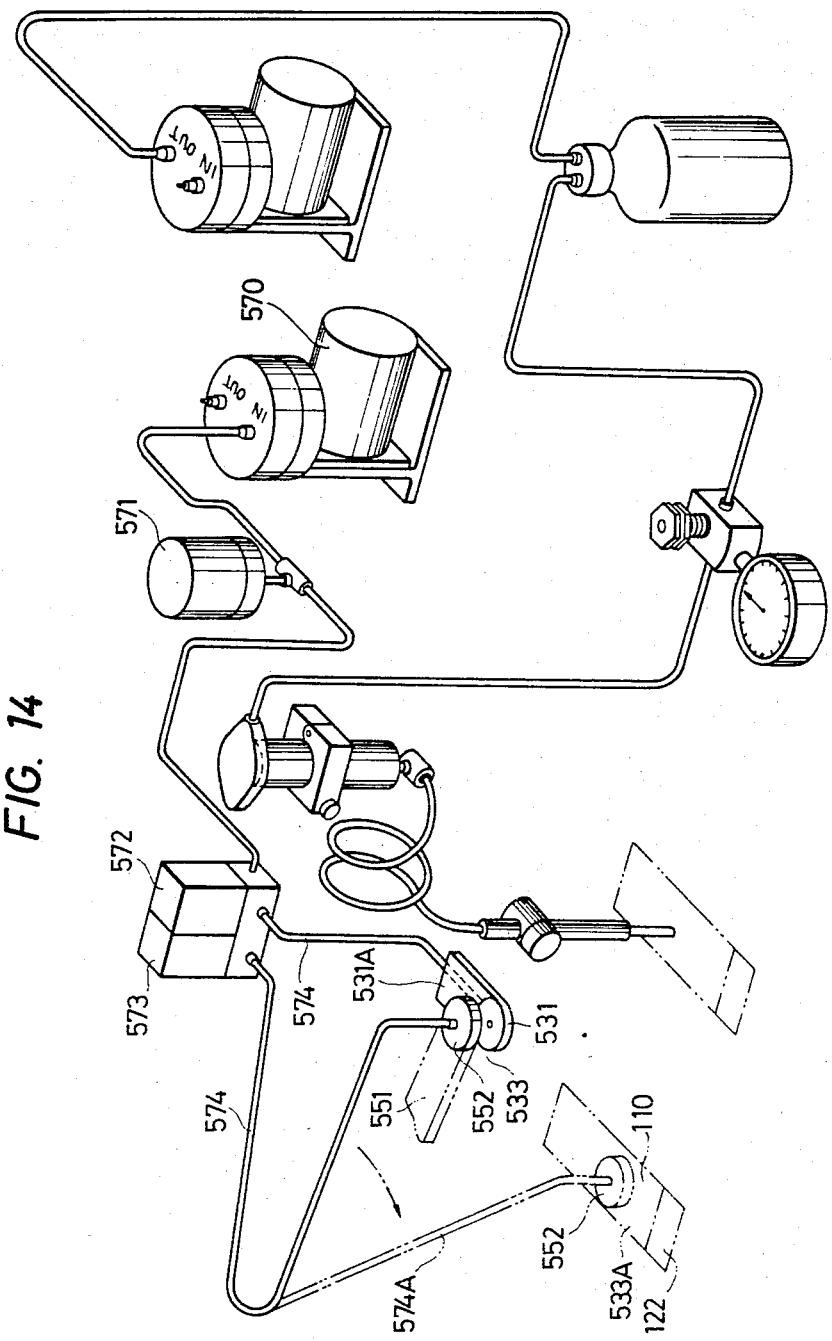
FIG. 14 is a perspective view showing an example of the structure of a vacuum supply mechanism.

FIG. 14 shows an example of the mechanism used for supplying a reduced pressure to the glass cover sorting supplying device 500, in which 570 is a vacuum pump, 517 is a vacuum switch for detecting when the supplied negative pressure is above a certain pressure and then switching on a warning device, 572 is an electromagnetic valve associated with the suction disc 531 of the extraction mechanism, and 573 is an electromagnetic valve for the suction disc 552 of the transfer mechanism. Further, 531A is an arm for reciprocating the suction disc 531 along the parallel groove 519 shown in FIG. 12. A suction tube 574 extends from the suction disc 531 through the arm 531A and is connected to the electromagnetic valve 572. FIG. 14 shows the state where both the suction discs 531 and 532 are at the transfer position 533, with the suction tube 574 from the suction disc 552 being connected to the electromagnetic valve 573. The suction tube 574A illustrated by broken lines corresponds to the state where the suction disc 552 has moved to the supply position 533A.

In the thus-arranged vacuum supply mechanism, by switching the negative pressure generated by the vacuum pump 570 between the electromagnetic valves 572 and 573, the negative pressure can be supplied to either one of the suction discs 531 and 552 to cause a suction operation. During the extraction operation by the suction disc 531 and the arm 531A, the negative pressure is supplied to the suction disc 531 by opening the valve 572 and closing the valve 573. After the time of transfer position 533, the vacuum pressure is switched to the suction disc 552 by closing the electromagnetic valve 572 and opening the electromagnetic valve 573.

Figure 15A:
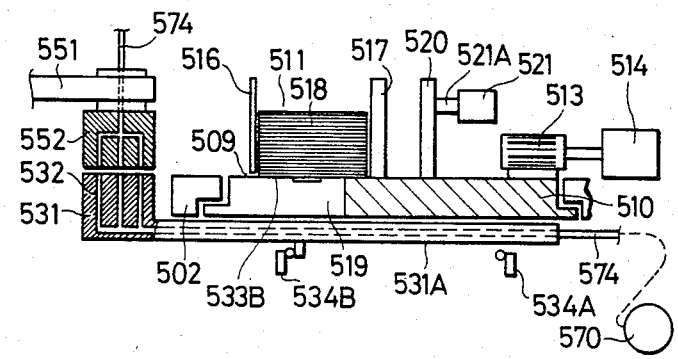
FIGS. 15(a) through 15(e) are explanatory views showing step by step a series of operations of the glass cover sorting/supplying device.
Figure 15B:
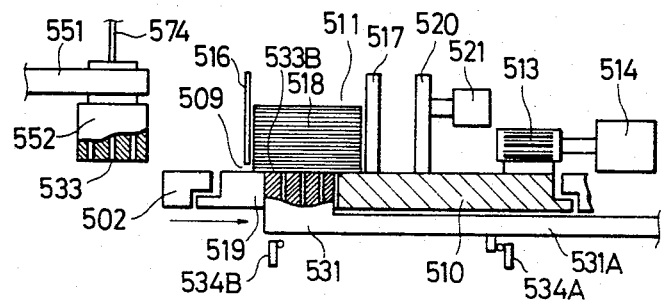
Figure 15C:
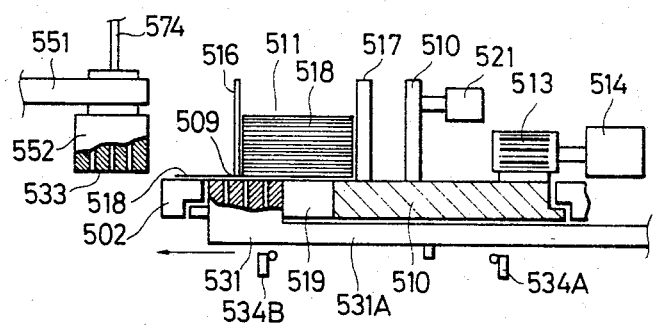
Figure 15D:
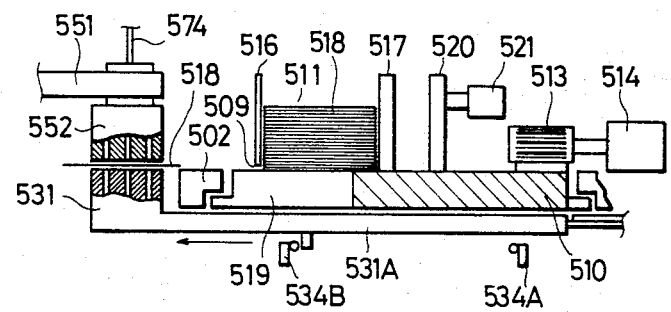

Then, a series of operations in the thus-arranged glass cover sorting/supplying device 500 will be described with reference to FIGS. 15(A) through 15(B). When the sorter 510 is started by a sorter drive motor, the contact roller 521A of the selection switch 521 comes successively into contact with the position detection pins (520D, 520C, 520B and 520A, in that order). When the position detection pin (520A to 520D) corresponding to the selected area 511 contacts the contact roller 521A, the sorter driver motor stops, terminating the movement of the sorter 510. This state is shown in FIG. 15(A). At the same time, the suction disc 531, standing by in the transfer position 533, is guided to the attraction position 533B in response to the shifting of the arm 531A (see FIG. 15(B)) until the pin 5311 shown in FIG. 12 and coupled to the arm 531A actuates the limit switch 534A and attracts only the lowermost one of the glass covers 518. Then, when the arm 531A returns to the initial position (the position where the pin 5311 actuates the limit switch 534B), the suction disc 531 is returned again to the initial transfer position 533 (see FIGS. 15(C) and (D)). Here, because the gap 509 allowing passage of only one glass cover 518 is formed between the flash board 516 and the upper face of the sorter 510, the covers piled above the lowermost one are prevented by the flash board 516 from being pulled out. When the single cover is pulled out, the remaining glass covers drop along the pins 517 without disturbing the piled state.

Figure 15E:
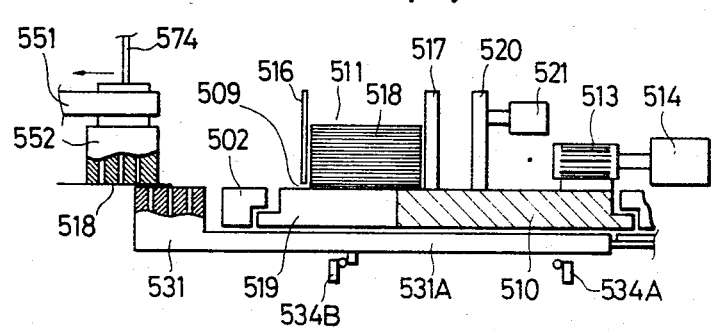

When the glass cover 518 is conveyed to the transfer position 533, supply of the negative pressure to the suction disc 531 is terminated, and switching between the electromagnetic valves 572 and 573 shown in FIG. 1 is performed. Thus, the vacuum pressure is supplied to the transfer suction disc 552 standing by slightly above the transfer position 553. Accordingly, the glass cover 518 is attracted by the suction disc 552 (see FIG. 15(E)) and shifted by the arm 551 to a position above the glass slide 110 (not shown) guided to the glass cover supply position, i.e., the binding position.

Below the glass slide 110 at the binding position there is provided the binding sealing device (hereinafter called the binding device) which causes up-down movement of the glass slide at an appropriate timing, thereby resulting in a binding of the glass slide 110 and the glass cover.

Figure 16:
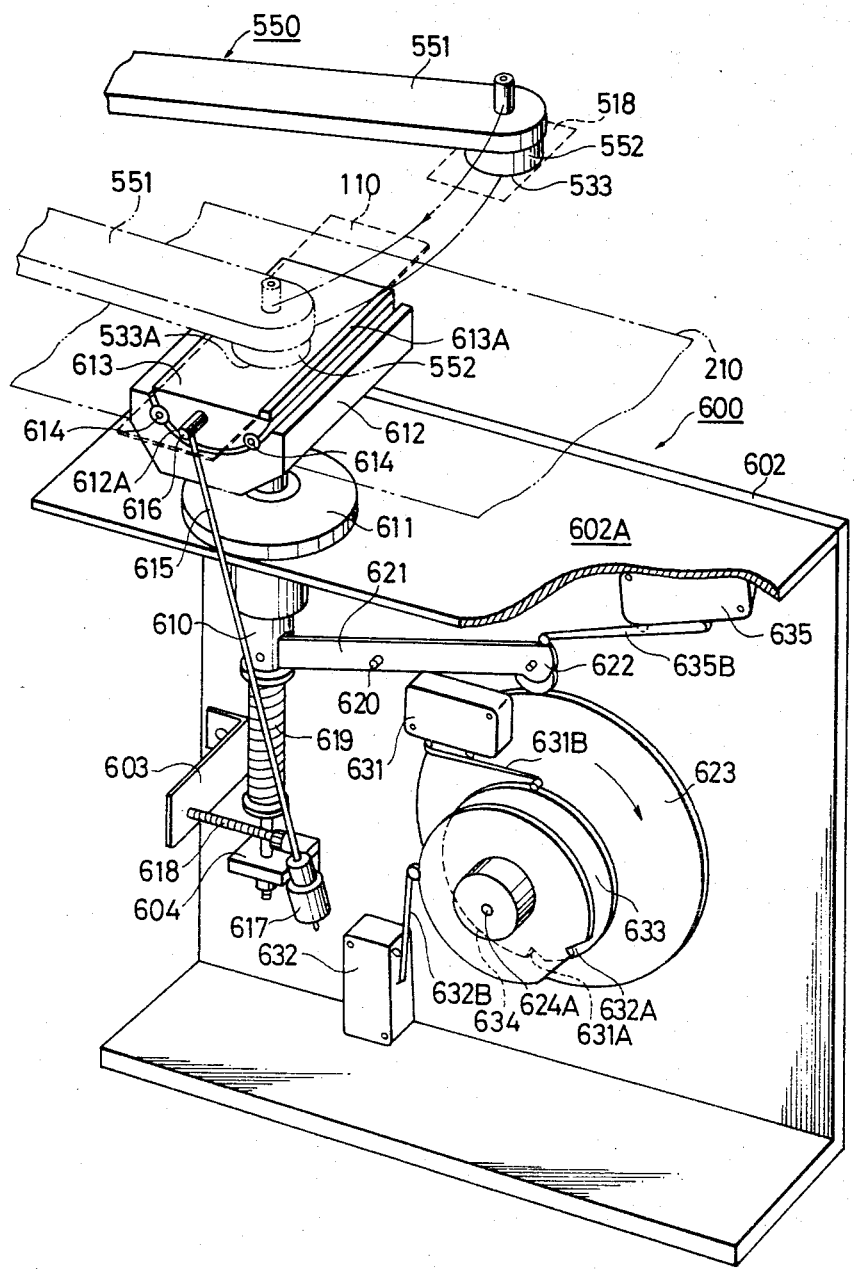
FIG. 16 is a perspective view showing the structure of a binding device of the automatic specimen sealing system of the invention.

FIG. 16 shows an example of the binding device 600. A support 602 of the binding device 600 is secured below the conveyor 210. On the upper plate 602A of the support 602 is mounted a spline socket 611 into which a lift shaft 610 is fitted and is movable up and down 612 is a support member secured to an upper end of the lift shaft 610. In the upper face of the support member 612 a groove 612A in the shape of an arc in cross section is formed, and in the groove 612A a swing member 613 corresponding in shape to the groove is received swingably via roller bearings 614. 615 is a swing rod secured via a fixing pin 616 to a side face of the support member 613. 617 is a weight mounted on a lower end of the swing rod via a bracket 603 to the support 602. A swing angle-adjusting member 618 of length adjustable is attached which is projecting toward the swing rod 615.

Figure 17A:
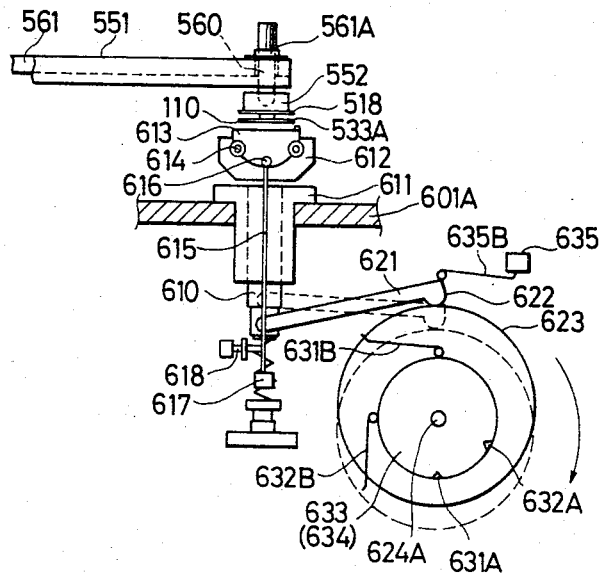
FIGS. 17(A) and 17(B) are a front view of the binding device and a side view of a cam device thereof, respectively.

By adjusting the length of the angle-adjusting member 618, the support member 613 can be held in an inclined state at an angle varying from about 1 degree to about 7 degrees, for example, via the swing rod 615 (see FIG. 17(A)). In normal operation, by adjusting the angle of inclination to the suport member 613, the glass slide 110 can be maintained in a state suitable for the binding operation as hereinafter described.

FIG. 17(A) shows the circumstances where the glass slide 110 on the conveyor 210 has just reached the position below the transfer mechanism 550. Specifically, in FIG. 17(a), 551 is an arm of the transfer mechanism 550. The suction disc 552 attached to the point of the arm 551 attracts the glass cover 518 supplied from the sorting/supplying device 500 and guides the same to a position above the glass slide 110 at the binding position 533A. FIG. 16 shows the circumstances where the arm 551 is rotated in the direction of the arrow from the transfer position 533. At this position 533, the glass cover 518 pulled out from the glass cover sorter 510 shown in FIG. 1 is transferred from the extraction mechanism 530 to the transfer mechanism 550 and is moved to the binding position 533A.

Figure 17B:
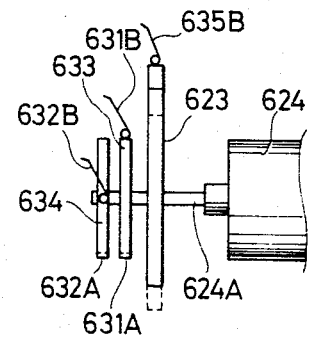

619 is a compression spring disposed between the lower end of the lift shaft 610 and a spring receiving member 604 attached to the support 602. Due to the spring force of the spring 619, the lift shaft 610 is biased upwardly. Further, to the lift shaft 610 a lever 621 is coupled which is rotatable about a shaft 620. At the other end of the lever 621 is formed a cam guide 622. 623 is an eccentric disc-like cam driven by a motor 624 (see FIG. 17(B)) with the cam 623 being secured coaxially to the motor 624 with the cam face thereof in contact with the cam guide 622. In response to rotation in the clockwise direction of the motor 624, the lever 621 swings about the shaft 620, thereby to move up and down the lift shaft 610.

To the motor shaft 624A, a disc cam 633 with a notch 631A and another disc cam 634 with a notch 632A are secured coaxially. By means of the notches 631A and 632A of the disc cams 633 and 634, the position detection switches 631 and 632 shown in FIG. 16 are actuated. 631B and 632B are operating levers of the switches 631 and 632, respectively.

635 is a position detection switch disposed in a predetermined relation to the cam guide 622 mounted on the lever 621. An operating lever 635B of the switch 635 is always in contact with the upper face of the cam guide 622. When the lever 621 is pushed up by the cam 623 to the highest position shown in FIG. 17(A), i.e., when the support member 613 is at the lowest position, the switch 635 is operated to detect this fact.

Further, in FIG. 17(A), 560 is a pushing member, illustrated by a broken line at the top of the arm 551.

This pushing member 560 is not mounted directly to the top of the arm 551, but is loosely fitted in a support hole 561A formed in the top of a branch arm 561 diverging from the arm 551. The top of the member 560 is formed with a smooth face.

The operation of the pushing member 560 will be described. This member is used to remove possible voids between the glass cover 518 and the glass slide 110 and to diffuse the adhesive. As shown in FIG. 17A, when the glass cover 518 has been carried to the binding position 533A, the pushing member 560 and the branch arm 561 supporting the former are at a retracted position different from the binding position 533A.

Next, the binding and sealing operation of the thus constructed binding device will be described with reference to FIGS. 13(A) through (F).

FIG. 18(A) shows the same state as that of FIG. 17(A), in which state the switch 635 used to detect the lowest position of the support member 613 (see FIG. 16) is in the ON state, whereby the motor 624 is energized to rotate the respective cams 623, 633 and 634 via the lift shaft 610 to lift the support member 613. As the result, as shown in FIG. 18(B), the glass slide 110 is lifted up by the support member 613 from the conveyor 210, and, at the time the edge of the glass slide 110 comes into contact with the edge of the glass cover 518 or near to the same, the notch 632A of the cam 634 is detected by the detection switch 632, whereby the motor 624 is stopped. The relative position between the switch 632 and the notch 632A is preadjusted for the foregoing operation. Further, at the inclined lower margin of the upper face of the support member 613 a slide stop 613A is provided. By this stop 613A the glass slide 110 is prevented from moving slidingly and is held at the predetermined position on the support member 613.

The state of FIG. 18(E) is sustained for a time, during which time the binding liquid drop 480A is diffused between the glass slide 110 and the glass cover 518 due to the capillary phenomenon and on account of the inclination of the glass slide 110. Following the above, as the supply of the negative pressure to the suction disc 552 is terminated, the glass cover 518 lies upon the glass slide 110 as shown in FIG. 19(C).

The suction disc 552 and the arm 551 having completed the supply of the glass cover 518 are immediately retracted, and the branch arm 561 and the pushing member 560 provided at the end thereof are moved to this position. This state is shown in FIG. 18(D). The suspended state of the support member 613 and the lift shaft 610 obtained in the condition of FIG. 18(B) is maintained to the time the state of FIG. 18(D) is realized. It is preferable to select the suspension time to be on the order of 2 to 3 seconds.

After the suspension time, the motor 624 is energized again to continue the lifting of the support member 613. At the time the notch 631A of the cam 633 aligns with the operating lever 631B of the position detection switch 631, the cam guide 622 of the lever 621 is held at its lowermost position by the eccentric disc cam 623, thereby to hold the support member 613 at its uppermost position. In this state the motor 624 is again stopped by operation of the switch 631.

This state is shown in FIG. 18(E). Because the axial center of the pushing member 560 is different from the axial center of the swing rod 615, as the pushing member 560 is pushed lightly against the glass cover 518 toward the glass slide 110 by gravity, the support member 613 leans a little due to the eccentric force, as indicated in FIG. 18(E). This state is maintained for a period on the order of 2 to 3 seconds, for example.

After such a suspension time related to the pushing operation, the motor 624 is energized again to lower the support member 613, the glass slide 110 is returned to the conveyor 210, and the support member returns to its initial inclined state, during which time the branch arm 561 and the pushing member 560 at the point of the former are moved by means of the link mechanism for moving the arm 551. FIG. 18(F) shows the state when the support member 613 and the lift shaft 610 have returned to the initial conditions as the result of the foregoing operations, corresponding to the state of FIG. 18(A).

In this way, even though air may be present between the glass cover 518 and the glass slide 110, it is possible to force such air outwards in all directions from the point of the pushing member 560 by the pushing operation during the foregoing suspension time. If such removal of air is insufficient, this can be easily overcome by increasing the weight of the pushing member 560.

Figures 19A, 19B:
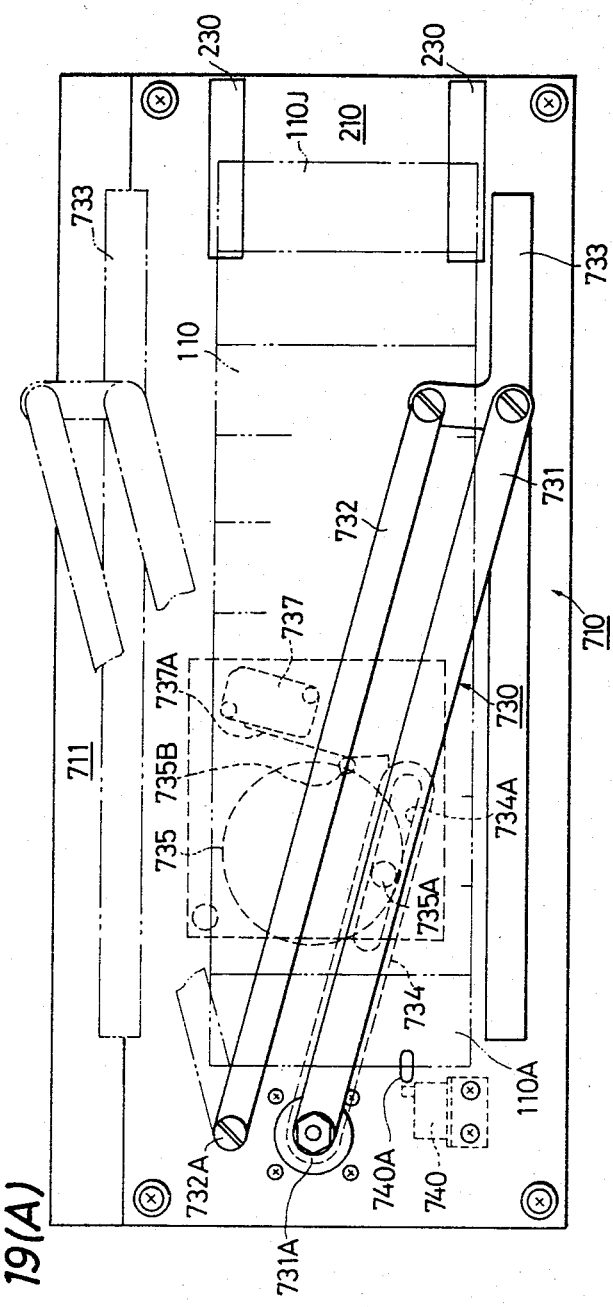
FIGS. 19(A) and 19(B) are, respectively, a plan view and a side view, partially cut away, showing a slide assembly area and the structure of a pushing mechanism in a housing device of the automatic specimen sealing system of the invention.

Next, the storage device 700 for storing the glass slides 110 having completed the specimen sealing processes as described above will be described. FIGS. 19(A) and 19(B) show the slide assembly area 710 and an example of a pushing mechanism provided around the former, in which the glass slides 110 conveyed along the conveyor 210 by means of the roller chain 230 from the right side in the drawing are pushed out successively into the slide assembly area 710, and, until ten slides have been accumulated, the slides are stored in side-by-side positions.

Reference numeral 730 indicates the pushing mechanism, which includes a link mechanism having parallel rods 731 and 732 and a wiper 733 coupled mutually in the turning pair fashion, the parallel rods 731 and 732 are rotatable about shafts 731A and 732A, respectively. Further, to the portion of the shaft 731A on the back side of a base plate 711 is attached an arm 734 which has a sliding groove 734A. Into this groove 734A a pin 735A of a rotary plate 735 is slidably fitted. The rotary plate 735 is rotated by a motor 736 mounted below the former. The rotary plate 735 is provided with a notch 735B, with which an operating lever 737A of a limit switch 737 can be engaged. That is, when the rotary plate 735 is driven by the motor 736 through one complete revolution and the link mechanism assumes the position shown in FIG. 19(A), the operating link 737A engages the notch 735B and the limit switch 737 stops the motor 738.

740 is a limit switch used to detect the accumulation of the glass slides 110. Although a limit switch is employed in the described embodiment, other types of sensors for position detection can be employed to energize the motor 736. The limit switch 740 has an operating pin 740A projecting beyond the base plate 711. As the glass slides 110 are pushed out successively into the slide assembly area 710 on the base plate 711, when the tenth glass slide 110J has been pushed out, the leading glass slide 110A abuts the operating lever 740A.

Besides the thus-arranged slide assembly area 710 and pushing mechanism 730, in the upper portion of FIG. 19(A) the tray 750 for the sealed specimen is provided abutting upon the base plate 711. When ten glass slides 110, each having a specimen sealed thereto, have been accumulated in the slide assembly area 710, the glass slides 110A through 110J in parallel alignment are swept away by the pushing mechanism 730 without need for further alignment modification.

Figure 20A:
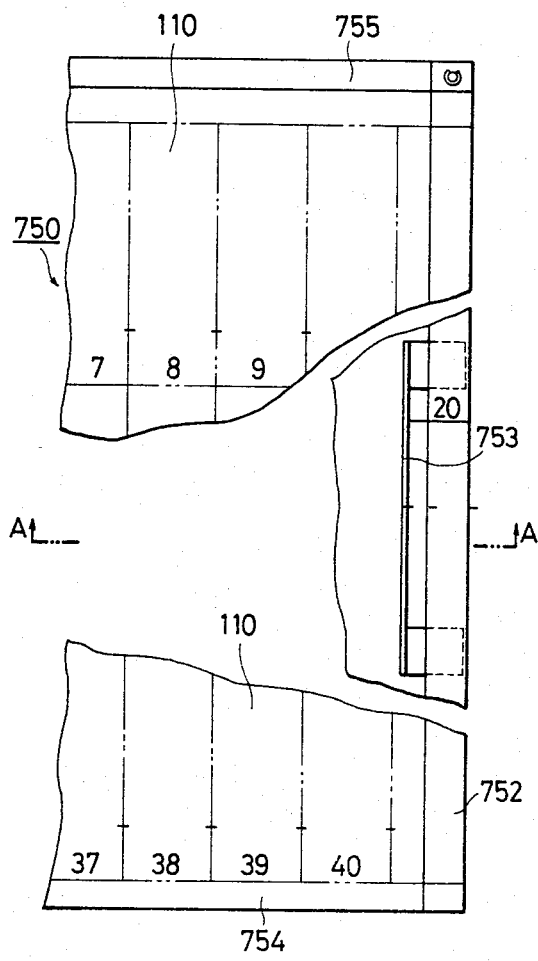
FIGS. 20(A) and 20(B) are a partial plane view and a side view, respectively, showing the structure of a tray in the housing device.
Figure 20B:
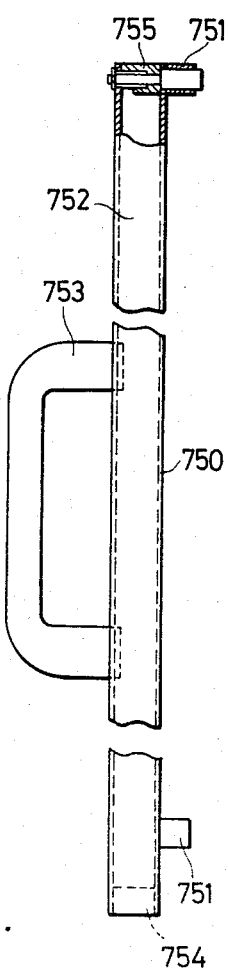
Figure 20C:
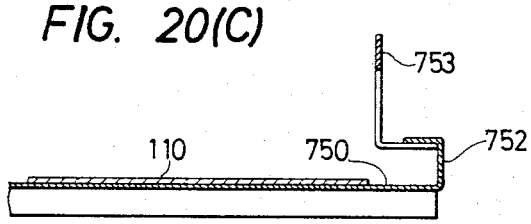
FIG. 20(C) is a sectional view taken along a line A—A in FIG. 20(A)

FIGS. 20(A), 20(B) and 20(C) show schematically the tray 750. Underside the tray 750 and disposed horizontally are attached frames 751. The tray is arranged in a certain tray rest position with the frames 751. Both sides of the tray 750 are bent to form sidewalls 752, and to each sidewall is attached a handle 753. Further, on the rear end is mounted a fixed stop member 754, and on the front end is mounted a vertically movable stop member 755.

Figures 21, 22:
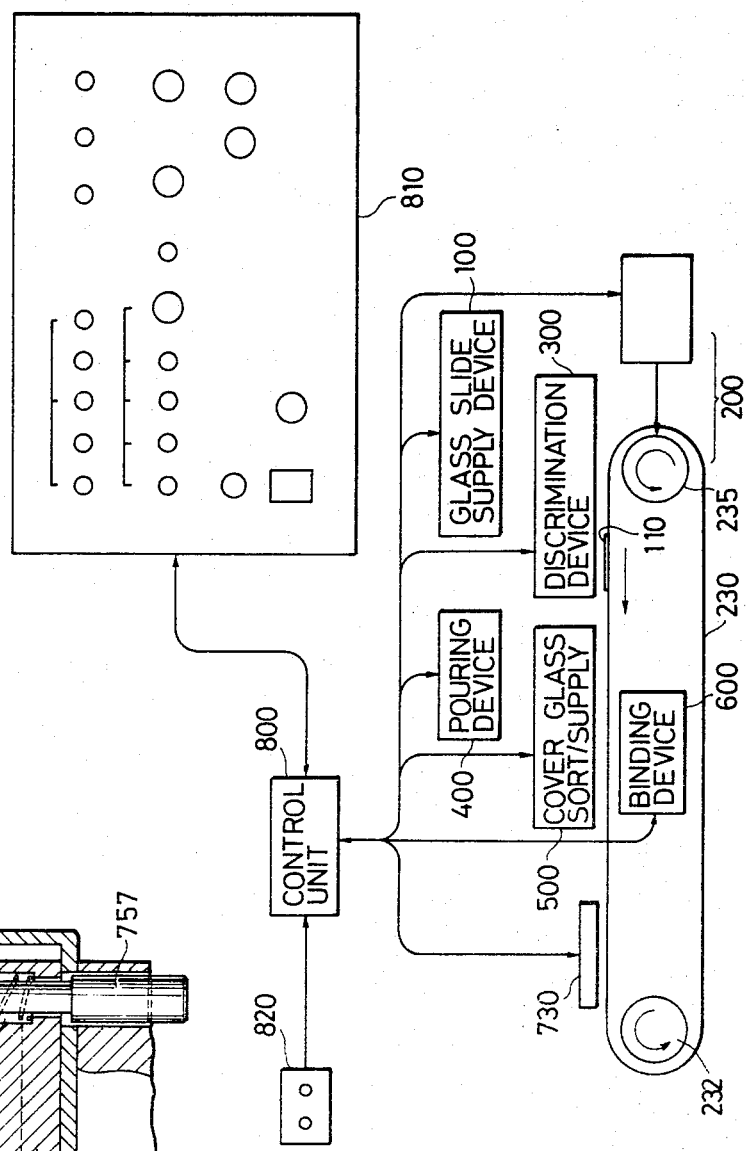
FIG. 21 is a sectional view showing the structure of a lock plate moving mechanism for the tray.
FIG. 22 is a block diagram showing a control system of the automatic specimen sealing system of the invention.

FIG. 21 shows the movable mechanism for the stop member 755 provided at the front end. In the both side ends of the member 755, shouldered through-holes 756 are formed. In these through-holes 756, thin portions of stepped lift rods 757 are fitted. 758 is a lock washer attached to the upper end of the lift rods 757 and 759 is a lock nut. 760 is a coil spring provided around the lift rod 757 and between the sidewall 752 and a shoulder portion of the through-hole 756. By providing at both sides of the front end of the tray 750 the movable mechanism for the stop member, to move the tray 750, the stop member 755 is moved down to the plane face of the tray 750 by means of the spring 760, as shown in the drawing, so that the slides 110 are prevented from sliding off the tray 750. When the tray 750 is placed on the plane board, the end of the rod 757 projecting downwardly below the frame 751 is pushed up from the plane board, and the rod 757 lifts up the stop member 755 while pushing against the spring force of the spring 760 (this state being shown in the broken lines in FIG. 21.). Accordingly, the sample or the slides 110 can be drawn out safely through the gap 761 between the face of the tray 750 and the lower face of the stop member 755.

Next, a series of storing operations in the thus-constructed glass slide storage device will be described with reference to FIG. 19.

In the example, the tray 750 can store 40 glass slides 110. Specifically, as the slides are pushed out successively into the slide assembly area 710, when ten slides have been accumulated, the limit switch 740 is turned on to operate the pushing mechanism 730, whereby the group of ten slides is pushed toward the tray 750. The link mechanism of the pushing mechanism 730, having completed such a pushing operation, returns to the stand-by position as shown in FIG. 19(A) and waits for accumulation of another ten slides. Each time ten glass slides are accumulated, the same operation is repeated, and when a total of 40 glass slides 110 has been stored in the tray 750, a series of the foregoing operations terminates.

Next, the mechanism for controlling several operations of the sealing processes in the present system will be described. FIG. 22 shows schematically the control system of the automatic specimen sealing system of the invention in which starting/stopping of the sealing operation is instructed by means of switches provided on the switch device 820. Further, on the console panel 810, as described above, there are provided a main power switch, various indicators, reset switches and the like, whereby the sealing operations can be monitored and various partial manipulations carried out.

Specifically, for each of the glass slides 110 put into the system from the glass slide supply device 100, the control device 800 causes the detection device 300, adhesive supply device 400, glass cover sorting/supplying device 500 and sealing device 600 to perform a series of processes, as will now be described in more detail with reference to FIG. 23.

Figures 23, 24A, 24B, 24C:
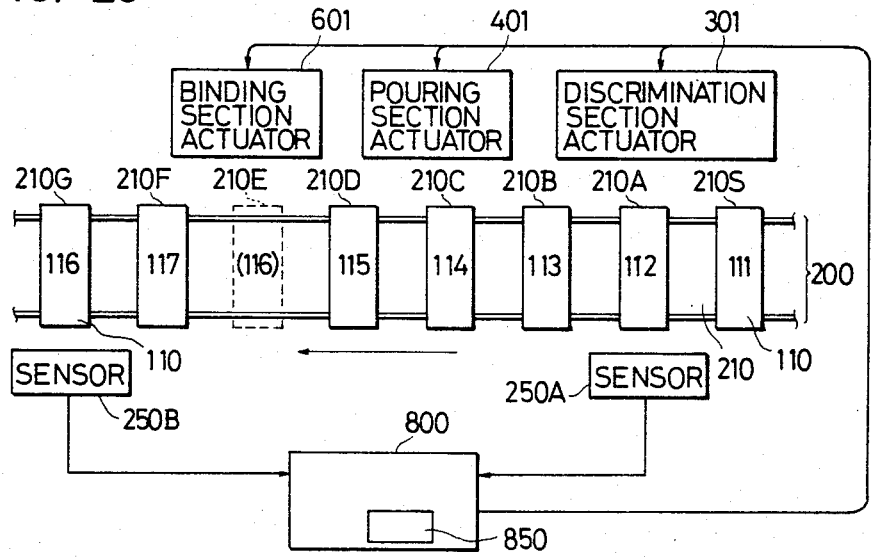
FIG. 23 is a block diagram for an explanation of the operation of the control mechanism.
FIGS. 24(A) through 24(C) are block diagrams showing the operating mode of each block in a memory device wherein data is shifted.

In FIG. 23, 111 through 118 are the glass slides supplied onto the conveyor 210 by the conveyor device 200. That is, the glass slides 110 or 111 through 118, are dropped onto the conveyor 210 at a fixed time interval from the glass slide supply device 100 (see FIG. 1) located on the right side in the drawing. These glass slides 110 are conveyed leftwardly one after another by the claws 231 of the roller chain 230 shown in FIGS. 6(A) and 6(B) at a certain pitch, and, as shown in FIG. 23, they are shifted step by step from position 210S to positions 210A, 210B, . . . , 210G on the conveyor 210.

In FIG. 23, 310 is an actuator for initiating the process of the specimen detection device 300, 401 is an actuator for initiating the process of the adhesive supply device 400, and 601 is an actuator for initiating the process of the sealing device 600, which actuators are operated in accordance with a program based on a flowchart described hereinafter to cause the devices 300, 400 and 600 to execute their processes.

250A and 250B are glass slide sensors disposed at position 210A and position 210G along the conveyor 210 (see FIG. 1). The presence/absence of the slides is detected by the sensors 250A and 250B at each position 210A through 210G along the conveyor 210.

Further, in the control device 800 is included a memory 800 having memory blocks whose memory contents are shiftable. Assuming that glass slides 110 are present at positions 210S to 210G as shown in FIG. 23, respective blocks A through G in the memory 850 representing positions 210A through 210G store respective data points 1 through 8 corresponding to glass slide numbers 112 through 118 and respective detection signals (logic signals "1" and "0") representing the presence/absence of the glass slides in the form of binary signals.

In the example shown in FIG. 23, the glass slide 116 is not present at position 210E on the conveyor 210, i.e., at the position for the binding section actuator 601, thus, the detection signal at block E is "0". On the other hand, the glass slide 112 at position 210A has been detected by the sensor 250A so that a slide detection signal "1" is stored.

Under the foregoing circumstances, as the next glass slide 100 is supplied and the glass slides 111 through 118 at respective positions 210S through 210G as shown in FIG. 23 move leftwardly one step, the data points in the memory 850 are also shifted leftwardly one bit position. That is, as shown in FIG. 24(B), the preceding memory value "8/1" in block G is shifted out and disappears, whereas the value "1" of the glass slide 110 and the detection signal "1" are inputted into block A.

Figure 25:
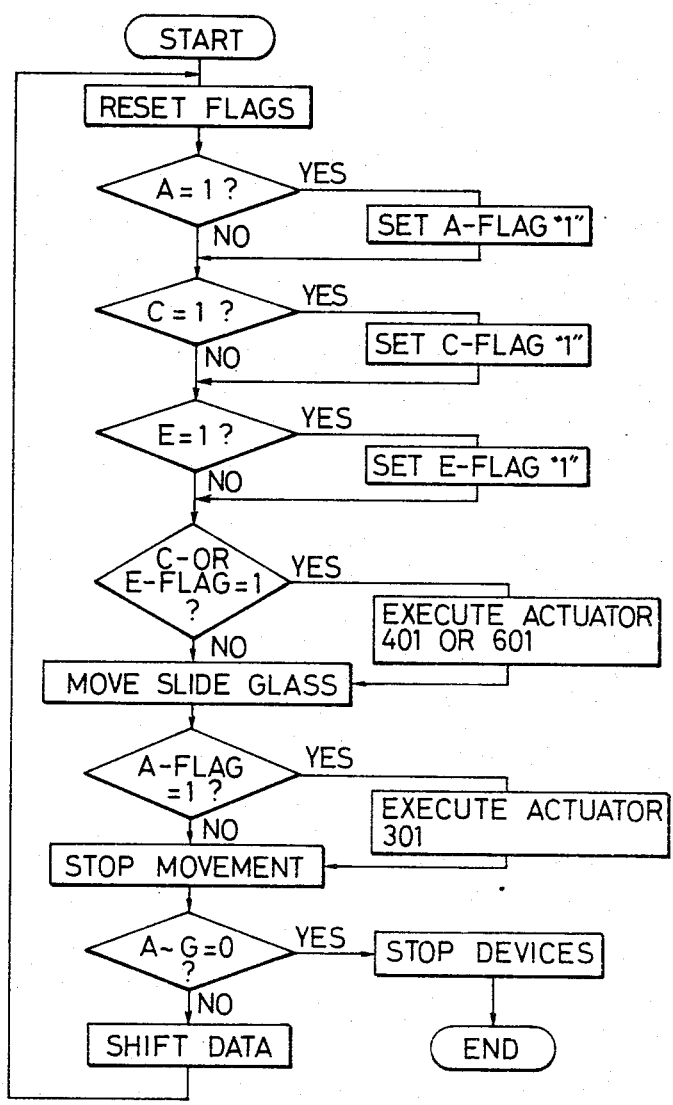
FIG. 25 is a flowchart showing the process with which the system is controlled using the memory device.

Assuming that the respective glass slides 111 through 117 are present at positions 210A through 210G, the control unit 800 searches the data in the memory 850 and sets flags for execution of the processes at blocks A and C because the detection signal "1" has been inputted to blocks A and C (see FIG. 25).

In the automatic specimen sealing system of this invention, the processes performed while the conveyor device 200 is moving and the processes performed when the conveyor device 200 is stopped (the suspension time period) are established in accordance with sequence control. For example, the process to discriminate the size of a specimen is performed while the glass slide 110 is moving from position 210A to position 210B, the pouring process to supply the adhesive onto the glass slide 110 is performed during the suspension time of the conveyor device 200 at position 210C, the glass cover sorting/supplying process to sort the covers and to supply them onto the slides 110 is performed mainly during the suspension period preceding the slides being shifted to position 210E, and the sealing process by the sealing device 600 is performed during the suspension period at position 210E.

Next, the control operation according for the thus-arranged sequential control mechanism will be described with reference to the flowchart of FIG. 25. It is assumed that each glass slide 110 has moved one step from the state showing in FIG. 23 and is now stopped. At first, flags are reset. Because the signal has been input in the memory 850 as shown in FIG. 24(B) and the detection signal in block A is "1", an A-flag for instructing the specimen detection section 300 to perform the discrimination process is set.

If the detection signal of block A is "0", the A-flag is not established and the detection signal of block C is detected as to whether it is "1" or not. Because the detection signal is "1" in the preset example, a C-flag for causing the adhesive supply device 400 to perform the pouring process is set. Then, upon searching block E, the detection signal is found to be "1", whereupon an E-flag for causing the sealing device 600 to perform the sealing process is set.

Further, in case the slides are present at respective positions as shown in FIG. 23, for example, in the memory 850 are stored the signals as shown in FIG. 24(A) and the detection signal "0" is found upon searching block E so that the E-flag is not set.

In this way, as the result of searching and in response to the C-flag being set, during this suspension period the pouring process is executed via the pouring section actuator 401 and the binding sealing process is executed via the binding section actuator 601. Subsequently, each glass slide 110 is moved one set position by the conveyor device 200, during which the size discrimination process for the specimen 121 is executed via the discrimination section actuator 301 because the A-flag has been set.

In the manner described above, through repetition of moving/stopping of the glass slides 110, the various processes are executed at respective predetermined positions. FIG. 24(C) shows the data in respective blocks A through G in the memory 850 obtained after the six steps of movement of the glass slide arrangement shown in FIG. 23 through the repetition of the foregoing processes.

As shown in FIG. 23, the glass slide sensor 250B located at position 210G on the conveyor 210 detects the presence/absence of a glass slide 110 conveyed to this position 210G. Then, if the detection signal from the sensor 250B indicates "presence of slide", the "1" signal is output when the glass slide 110 has moved six steps from the state shown in FIG. 23. The signal "1" from the sensor 250B is compared in the control device 800 with data "2/1" stored in block G of the memory 850. As a result, it is found that the glass slide 112 previously at position 210A in FIG. 23(A) has been conveyed to position 210G without difficulty, and thus the conveying and processing are continued.

On the other hand, if the signal from the sensor 250B indicates "absence of slide" and the "0" signal is output, this means that the glass slide 112 corresponding to the data "2/1" shifted to block G in the memory 850 at the time of comparison has not detected, and it is determined that the glass slide 112 was subjected to some fault, for example, it may have left from the conveyor 210 at some point. Accordingly, the control device 800 will output an abnormal signal or instruct the conveyor device 200 to stop or take some other necessary step.

Figure 26:
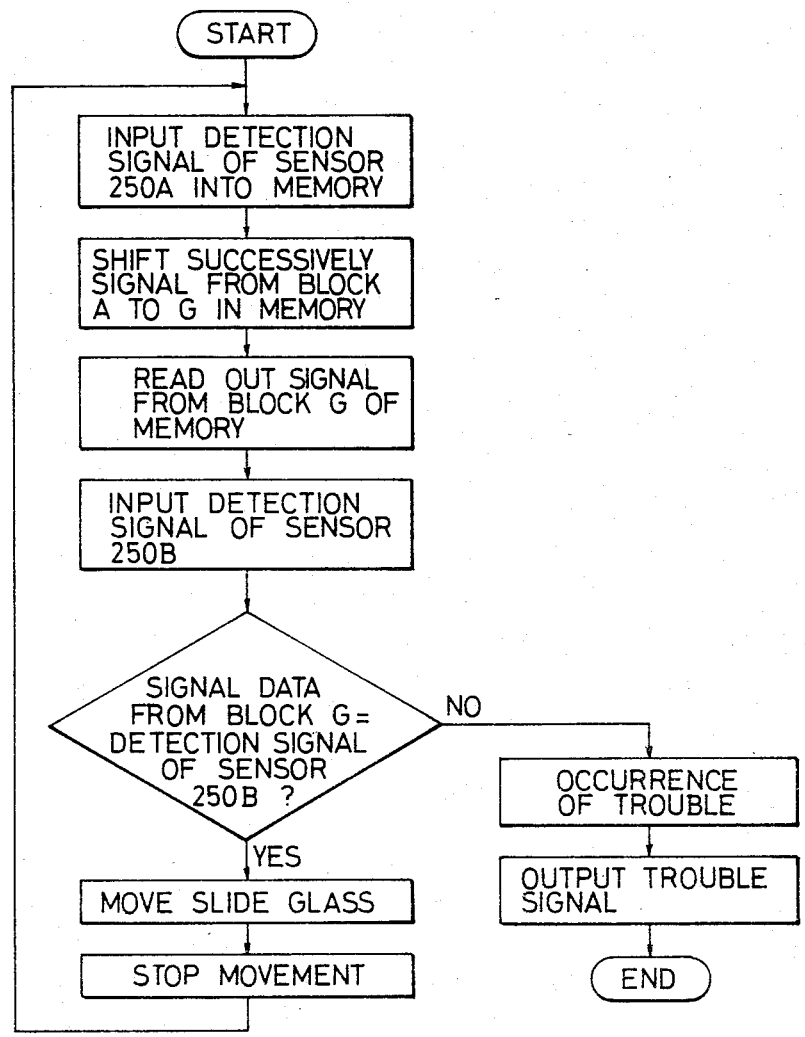
FIG. 26 is a flowchart showing how a fault on a glass slide is detected by the control mechanism.

FIG. 26 is a flowchart illustrating the processes of detecting occurrence of faults along the conveyor 210 by means of detecting the presence/absence of slides as above.

In summary, as described hereinabove, the present invention resides in an automatic specimen sealing system including a glass slide supply device for ejecting glass slides one after another at a predetermined time interval to predetermined positions on a conveyor at a certain orientation thereon, a conveyor device for conveying the slides supplied onto the conveyor, a specimen detection device for detecting optically the size of the specimens on the slides being conveyed along the conveyor, an adhesive supply device for supplying a liquid adhesive onto the slides in response to the size of the specimen, a glass cover sorting/supplying device for supplying glass covers of an appropriate size in response to the sizes of the specimens onto the corresponding slides conveyed to a supply position, a sealing device for lifting up the slides from the supply position to effect sealing between the slides and the covers supplied from the glass cover sorting/supplying device and then returning again the slides to the supply position on the conveyor, a storage device for moving in parallel a predetermined number of the glass slides having been bound and ejected from by the conveyor device to house them, and a control unit for controlling these devices, that is, the glass slide supply device, the specimen detection device, the adhesive supply device, the glass cover sorting/supplying device, the sealing device, the storage device and the conveyor device. The control unit computes the size of the specimens on the basis of a data signal from the detection device and applying a sorting signal to the adhesive supply device and the glass cover sorting/supplying device thereby to effect operations corresponding to the size of the specimen. Also, the control unit detects whether slides have been subjected to a fault condition.

Accordingly, the automatic specimen sealing system of the present invention operates automatically in such a manner that the glass slides are successively supplied onto the conveyor, the size of the specimen is detected by the detection device and the control unit in the course of conveying, liquid adhesive and a glass cover in an amount and in a size corresponding to the size of the specimen are supplied onto the glass slide, and the glass slide having the specimen sealed is housed.

Therefore, in accordance with the invention, sealing operations are completely automated, the selective use of expensive glass covers lowers costs and inclusion of air is prevented, thereby resulting in sealed specimens of high quality.

We claim:

1. An automatic specimen sealing system comprising:
   a conveyor for conveying said glass slides;
   a glass slide supplying device for ejecting glass slides sequentially at predetermined time intervals onto said conveyor at a predetermined orientation;
   a discriminating device for detecting optically the size of specimens on said glass slides being conveyed on said conveyor;
   a pouring device for supplying an adhesive liquid onto said glass slides in an amount determined by the size of the respective specimens;
   a glass cover sorting/supplying device for supplying glass covers of a size determined by the size of said specimens to said glass slides conveyed to a supply position on said conveyor;
   a binding device for lifting up said glass slides from said supply position to effect sealing of said specimens between said glass slides and said glass covers and then returning again said glass slides to said supply position;
   an assemblying device for moving simultaneously a predetermined number of said glass slides having been returned to said supply position and ejected by said conveyor to assemble said slides in a tray; and
   a control unit for effecting in synchronization with movement of said conveyor processing of said glass slide supplying device, said discriminating device, said pouring device said glass cover sorting/supplying device, and said sealing device.

2. The automatic specimen sealing system as claimed in claim 1, wherein said control unit comprises: sensors positioned at an upper course of said discriminating device and at an upper course of said assembling device along said conveyor for detecting presence/absence of said slides; and a memory device, said memory device storing data representing positions of said slides for each movement of said slides along said conveyor, whereby data representing the presence/absence of said glass slides is detected by said sensors, said data is shifted in synchronization with each said movement, and operations of said discriminating device, said pouring device, said glass cover sorting/supplying device and said sealing device are controlled through said control unit, and when a fault occurs on a glass slide on said conveyor, said fault is detected from said data in said memory device.

* * * * *